US012240790B2

(12) United States Patent
Dudkin et al.

(10) Patent No.: US 12,240,790 B2
(45) Date of Patent: Mar. 4, 2025

(54) RADIOLABELING OF POLYPEPTIDES

(71) Applicant: Janssen Biotech, Inc., Horsham, PA (US)

(72) Inventors: Vadim Dudkin, Chalfont, PA (US); Shalom Goldberg, Merion Station, PA (US); Joseph Erhardt, Sellersville, PA (US); Rhys Salter, Doylestown, PA (US); Theresa McDevitt, Warminster, PA (US)

(73) Assignee: Janssen Biotech, Inc., Horsham, PA (US)

( * ) Notice: Subject to any disclaimer, the term of this patent is extended or adjusted under 35 U.S.C. 154(b) by 829 days.

(21) Appl. No.: 16/955,094

(22) PCT Filed: Dec. 17, 2018

(86) PCT No.: PCT/US2018/065913
§ 371 (c)(1),
(2) Date: Jun. 18, 2020

(87) PCT Pub. No.: WO2019/125982
PCT Pub. Date: Jun. 27, 2019

(65) Prior Publication Data
US 2021/0017099 A1    Jan. 21, 2021

Related U.S. Application Data

(60) Provisional application No. 62/599,830, filed on Dec. 18, 2017.

(51) Int. Cl.
| | | |
|---|---|---|
| *A61K 39/00* | (2006.01) | |
| *A61K 51/10* | (2006.01) | |
| *A61P 35/00* | (2006.01) | |
| *C07B 59/00* | (2006.01) | |
| *C07K 16/30* | (2006.01) | |

(52) U.S. Cl.
CPC ........ *C07B 59/008* (2013.01); *A61K 51/1072* (2013.01); *A61K 51/1096* (2013.01); *A61P 35/00* (2018.01); *C07K 16/3069* (2013.01); *A61K 2039/505* (2013.01); *C07B 2200/05* (2013.01); *C07K 2317/41* (2013.01)

(58) Field of Classification Search
CPC .............................................. A61K 2039/505
See application file for complete search history.

(56) References Cited

U.S. PATENT DOCUMENTS

| | | |
|---|---|---|
| 2013/0266512 A1 | 10/2013 | Fox et al. |
| 2014/0024929 A1 | 1/2014 | Gorges et al. |
| 2014/0249296 A1 | 9/2014 | Ploegh et al. |
| 2015/0024614 A1 | 1/2015 | Gao |
| 2015/0246146 A1 | 9/2015 | Agnew et al. |
| 2017/0029700 A1 | 2/2017 | Taniguchi et al. |
| 2017/0297008 A1 | 10/2017 | Zeng |

FOREIGN PATENT DOCUMENTS

| | | |
|---|---|---|
| JP | 2014506869 A | 3/2014 |
| WO | 98/23643 A1 | 6/1998 |
| WO | 1998023643 | 6/1998 |
| WO | 2008/027944 A2 | 3/2008 |
| WO | 2011/008990 A1 | 1/2011 |
| WO | 2012049624 A1 | 4/2012 |
| WO | 2012075361 A2 | 6/2012 |
| WO | 2012096760 A1 | 7/2012 |
| WO | 2015057066 A1 | 4/2015 |
| WO | 2016142702 A1 | 9/2015 |
| WO | WO 2015073746 A1 | 11/2015 |
| WO | WO 2015176056 A1 | 11/2015 |
| WO | 2016046793 A2 | 3/2016 |
| WO | 2017192605 A1 | 11/2017 |

OTHER PUBLICATIONS

Zeglis et al. (Bioconjug. Chem. Jun. 19, 2013; 24 (6): 1057-67).*
Jin et al. (Signal Transduct. Target Ther. Feb. 7, 2022; 7 (1): 39; pp. 1-28).*
Sharkey et al. (J. Nucl. Med. Jan. 2005; 46 (Suppl. 1): 115S-27S).*
Schmittgen et al. (Int. J. Cancer. Nov. 1, 2003; 107 (2): 323-9).*
Nováková et al. (Prostate. May 2017; 77 (7): 749-64; author manuscript; pp. 1-28).*
Almeida et al. (Angew Chem. Int. Ed. Engl. Mar. 5, 2012; 51 (10): 2443-7).*
Chen et al. (ACS Med. Chem. Lett. Sep. 19, 2012; 3 (12): 1019-23).*
Khatwani et al. (Bioorg. Med. Chem. Jul. 15, 2012; 20 (14): 4532-9).*
Morais et al. (Drug Discov. Today Technol. Dec. 2018; 30: 91-104).*
Wei et al. (Chem. Rev. Apr. 22, 2020; 120 (8): 3787-3851).*
Chomet et al. (Bioconjug. Chem. Jul. 21, 2021; 32 (7): 1315-1330).*
Jeon et al. (Bioorg. Med. Chem. Jul. 1, 2015; 23 (13): 3303-8).*
International Search Report relating to corresponding PCT Patent Application No. PCT/US2018/065913. Mailing Date of International Search Report: Mar. 26, 2019.
Written Opinion relating to corresponding PCT Patent Application No. PCT/US2018/065913. Mailing Date of Written Opinion: Mar. 26, 2019.
Agarwal, P. and C.R. Bertozzi, "Site-specific antibody-drug conjugates: the nexus of bioorthogonal chemistry, protein engineering, and drug development.", *Bioconjug Chem*, 2015, pp. 176-192, vol. 26(2).
Deal et al., "Improved in vivo stability of actinium-225 macrocyclic complexes.", *J Med Chem*, 1999, pp. 2988-2992, vol. 42(15).
Debets et al., "Bioconjugation with strained alkenes and alkynes.", *Acc Chem Res*, 2011, pp. 805-815, vol. 44(9).

(Continued)

*Primary Examiner* — Stephen L Rawlings
(74) *Attorney, Agent, or Firm* — Ice Miller LLP

(57) ABSTRACT

Improved methods of radiolabeling antibodies using click chemistry are described. Also described are pharmaceutical compositions and uses related to the radiolabeled antibodies produced by the methods.

23 Claims, 7 Drawing Sheets
Specification includes a Sequence Listing.

(56) References Cited

OTHER PUBLICATIONS

Dennler et al., "Transglutaminase-based chemo-enzymatic conjugation approach yields homogeneous antibody-drug conjugates.", *Bioconj Chem*, Mar. 19, 2014, pp. 569-578, vol. 25(3).

Evans, R., "The Rise of Azide-Alkyne 1,3-Dipolar 'Click' Cycloaddition and its Application to Polymer Science and Surface Modification.", Australian Journal of Chemistry, 2007, pp. 384-395, vol. 60.

Kolb et al., "Click Chemistry: Diverse Chemical Function from a Few Good Reactions.", Angewandte Chemie International Edition, 2001, pp. 2005-2021, vol. 40.

Kraeber-Bodere et al., "A pretargeting system for tumor PET imaging and radioimmunotherapy.", *Front Pharmacol*, Mar. 31, 2015, Article 54.

Kwekkeboom et al., "[$^{177}$Lu-DOTA$^0$, Tyr$^3$]octreotate: comparison with [$^{111}$In-DTPA$^0$]octreotide in patients.", *Eur J Nucl Med.*, Sep. 2001, pp. 1319-1325, vol. 28(9).

Laverman et al., "In-depth evaluation of the cycloaddition-retro-Diels-Alder reaction for in vivo targeting with [$^{III}$In]-DTPA-RGD conjugates.", Nuclear Medicine and Biology, Oct. 1, 2009, pp. 749-757, vol. 36(7), Elsevier, NY, US, XP026545226.

Li et al., "Preparation of well-defined antibody-drug conjugates through glycan remodeling and strain-promoted azide-alkyne cycloadditions.", *Angew Chem Int Ed*, 2014, pp. 7179-7182, vol. 53(28).

Maguire et al., "Efficient 1-step radiolabeling of monoclonal antibodies to high specific activity with 225Ac for alpha-particle radioimmunotherapy of cancer.", *J Nucl Med*, 2014, pp. 1492-1498, vol. 55(9).

McDevitt et al., "Tumor therapy with targeted atomic nanogenerators.", *Science*, Nov. 16, 2001, pp. 1537-1540, vol. 294.

Miederer et al., "Realizing the potential of the Actinium-225 radionuclide generator in targeted alpha particle therapy applications.", *Adv Drug Deliv Rev*, 2008, pp. 1371-1382, vol. 60(12).

Pandya et al., "Zirconium tetraazamacrocycle complexes display extraordinary stability and provide a new strategy for zirconium-89-based radiopharmaceutical development.", *Chem Sci.*, 2017, pp. 2309-2314, vol. 8(3).

Spicer et al., "Selective chemical protein modification.", *Nature Communications*, 2014, 5:4740.

Thiele et al., "An Eighteen-Membered Macrocyclic Ligand for Actinium-225 Targeted Alpha Therapy.", *Angew Chem Int Ed*, Nov. 13, 2017, pp. 14712-14717, vol. 56(46).

Xiao et al., "Genetic incorporation of multiple unnatural amino acids into proteins in mammalian cells.", *Angew Chem Int Ed*, 2013, pp. 14080-14083, vol. 52.

Zeng et al., "New cross-bridged cyclam derivative CB-TE1K1P, an improved bifunctional chelator for copper radionuclides," Chem. Commun., 2014, 50, pp. 43-45.

Brechbiel, et al., "Bifunctional Chelates for Metal Nuclids," Q J Nucl Med Mol Imaging. Jun. 2008 ; 52(2): 166-173.

Laverman, et al., "In-depth evaluation of the cycloaddition-retro-Diels-Alder reaction for in vivo targeting with [111In]-DTPA-RGD conjugates," Nuclear Medicine and Biology, 36:749-757, 2009.

Li, et al., "Receptor-binding, biodistribution, and metabolism studies of 64Cu-DOTA-cetuximab, a PET-imaging agent for epidermal growth-factor receptor-positive tumors," Cancer Biotherapy & Radiopharmaceuticals. 23 (2):158-171, 2008.

Ning, et al., "Visualizing Metabolically-Labeled Glycoconjugates of Living Cells by Copper-Free and Fast Huisgen Cycloadditions," Angew Chem Int Ed Engl., 2008, 47(12): 2253-2255.

Zeng, et al., "New cross-bridged cyclam derivative CB-TE1K1P, an improved bifunctional chelator for copper radionuclides," Chem. Commun., 2014, 50:43-45.

Xu, et al., "Synthesis and evaluation of 64Cu-radiolabeled NOTA-cetuximab (64Cu-NOTA-C225) for immuno-PET imaging of EGFR expression," Chin J Cancer Res 2019;31(2):400-409.

Sletten, Ellen M., et al., "From Mechanism to Mouse: A Tale of Two Bioorthogonal Reactions," Accounts of Chemical Research, vol. 44, No. 9, pp. 666-675, 2011.

Zeng, Dexing, et al., "64Cu Core-Labeled Nanoparticles with High Specific Activity via Metal-Free Click Chemistry," AC Nano, vol. 6, No. 6, pp. 5209-5219, 2012.

\* cited by examiner

RADIOLABELING OF POLYPEPTIDES

CROSS-REFERENCE TO RELATED APPLICATIONS

This application is a U.S. national stage of PCT Application No. PCT/US2018/065913, filed on 17 Dec. 2018, and is entitled to priority pursuant to 35 U.S.C. § 119(e) to U.S. Provisional Patent Application No. 62/599,830, filed on 18 Dec. 2017, the disclosures of which are incorporated by reference herein in their entireties.

REFERENCE TO SEQUENCE LISTING SUBMITTED ELECTRONICALLY

This application contains a sequence listing, which is submitted electronically via EFS-Web as an ASCII formatted sequence listing with a file name "Sequence_Listing", creation date of Dec. 7, 2018, and having a size of about 13.2 kB. The sequence listing submitted via EFS-Web is part of the specification and is herein incorporated by reference in its entirety.

FIELD OF THE INVENTION

The invention relates to methods for radiolabeling polypeptides, such as antibodies. In particular, the invention relates to methods of using click chemistry to label a polypeptide with a radiometal ion. The invention also relates to pharmaceutical compositions and uses of the radiolabeled polypeptides.

BACKGROUND OF THE INVENTION

Alpha particle-emitting radionuclides have great promise for cancer therapy due to their combination of high energy with short-range action, providing the possibility of potent killing that is mostly localized to tumor cells (Kim, Y. S. and M. W. Brechbiel, An overview of targeted alpha therapy. *Tumour Biol,* 2012. 33(3): p. 573-90). Targeted delivery of alpha-emitters, using an antibody, scaffold protein, small molecule ligand, aptamer, or other binding moiety that is specific for a cancer antigen, provides a method of selective delivery of the radionuclide to tumors to enhance their potency and mitigate off-target effects. In common practice, the binding moiety is attached to a chelator which binds to the alpha-emitting radiometal to produce a radiocomplex. Many such examples use a monoclonal antibody (mAb) as the targeting ligand, to produce what is known as a radio-immunoconjugate.

Actinium-225 ($^{225}$Ac) is an alpha-emitting radioisotope that is of particular interest for medical applications (Miederer et al., Realizing the potential of the Actinium-225 radionuclide generator in targeted alpha particle therapy applications. *Adv Drug Deliv Rev,* 2008. 60(12):71-82). The 10-day half-life of $^{225}$Ac is long enough to facilitate radioconjugate production, but short enough to match the circulation pharmacokinetics of delivery vehicles such as antibodies. As such, $^{225}$Ac radioimmunoconjugates are of particular interest. Additionally, $^{225}$Ac decays in a series of steps that ultimately emits 4 alpha particles before reaching a stable isotope, $^{209}$Bi, thereby increasing the potency. Another radioisotope of interest for medical applications is Lutetium-177 ($^{177}$Lu), which emits both gamma-irradiation suitable for imaging and medium-energy beta-irradiation suitable for radiotherapy. It has been shown that $^{177}$Lu-labeled peptides demonstrate reduced normal tissue damage, and that $^{177}$Lu-labeling makes it possible to use a single radiolabeled agent for both therapy and imaging (Kwekkeboom D J, et al. [177Lu-DOTAOTyr3]octreotate: comparison with [111In-DTPAo]octreotide in patients. *Eur J Nucl Med.* 2001; 28: p. 1319-1325). Other radioisotopes that are used for therapeutic applications include, e.g., beta or alpha emitters, such as, e.g., thorium, radium, $^{32}$P, $^{47}$Sc, $^{67}$Cu, $^{77}$As, $^{89}$Sr, $^{90}$Y, $^{99}$Tc, $^{105}$Rh, $^{109}$Pd, $^{111}$Ag, $^{131}$I, $^{153}$Sm, $^{159}$Gd, $^{165}$Dy, $^{166}$Ho, $^{169}$Er, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{255}$Fm and $^{227}$Th. Other radioisotopes that are used for imaging applications include gamma-emitting radioisotopes, such as, e.g., $^{62}$Cu, $^{64}$Cu, $^{67}$Ga, $^{68}$Ga, $^{86}$Y, $^{89}$Zr, and $^{111}$In.

Previous clinical and pre-clinical programs have largely used 1,4,7,10-tetraazacyclododecane-1,4,7,10-tetraacetic acid (DOTA) for actinium chelation. However, it is known that DOTA chelation of actinium can be challenging (Deal, K. A., et al., Improved in vivo stability of actinium-225 macrocyclic complexes. *J Med Chem,* 1999. 42(15): p. 2988-92), and often requires either harsh conditions or high levels of DOTA per antibody. As a result, two different approaches—known as the "1-step" and "2-step" radiolabeling methods—have been utilized, each with their own drawbacks.

The "2-step" method, which includes 2 chemical steps involving actinium, was the first to be developed (McDevitt, M. R., et al., Tumor therapy with targeted atomic nanogenerators. *Science,* 2001. 294(5546): p. 1537-40). $^{225}$Ac was chelated by the bifunctional chelator (BFC) DOTA-isothiocyanate (DOTA-SCN) in high radiochemical yield (~95%) at pH 4.5-5 using 2 M acetate buffer at 55° to 60° C. for 30 min. Subsequently, the $^{225}$Ac-DOTA-SCN was reacted with the targeting antibody to produce the radioimmunoconjugate. The major drawback of the 2-step method is that ~90% of the SCN fails to survive the labeling conditions, thus ~90% of the input $^{225}$Ac is conjugated to nonreactive forms of DOTA that cannot be conjugated to the antibody. This results in not only low yield (typically only about 10%) and higher costs, but also lowered specific activity that can limit the efficacy of the final conjugate.

The "1-step" method was developed more recently for actinium (Maguire, W. F., et al., Efficient 1-step radiolabeling of monoclonal antibodies to high specific activity with 225Ac for alpha-particle radioimmunotherapy of cancer. *J Nucl Med,* 2014. 55(9): p. 1492-8). This method has only 1 chemical reaction step involving actinium. The DOTA-SCN was first conjugated to the antibody. The $^{225}$Ac was then chelated to the DOTA-mAb under mild conditions (37° C., pH 7.5), achieving up to 80% radiochemical yield. However, it was necessary to conjugate high levels of DOTA (~10 or more per antibody) to achieve high yields. The high chelator:antibody ratio (CAR), in this case the high DOTA:Ab ratio (DAR), species are more likely to have compromised immunoreactivity; furthermore, though the average DAR may be 10, it is likely that the $^{225}$Ac is chelating to populations with ratios even higher than the average. Thus, this method runs the risk of linking the $^{225}$Ac to the least active fraction of antibody-chelator conjugates. Furthermore, it is necessary to handle the antibody and DOTA-mAb conjugate under metal-free conditions to avoid chelation of common metals such as iron, zinc and copper, which introduces significant challenges into the production process.

Click chemistry is a chemical approach introduced by Sharpless in 2001 and describes chemistry tailored to generate substances quickly and reliably by joining small units together. See, e.g., Kolb, Finn and Sharpless Angewandte Chemie International Edition (2001) 40: 2004-2021; Evans, Australian Journal of Chemistry (2007) 60: 384-395). Coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition (e.g., 1,3-dipolar cycloaddition between an azide and an alkyne to form a 1,2,3-triazole linker); thiolyne addition; imine formation; Diels-Alder reactions between tetrazines and trans-cyclooctene (TCO); and Michael additions (e.g., maleimide addition).

Click chemistry reactions between alkynes and azides typically require the addition of a copper catalyst to promote the 1,3-cycloaddition reaction, and are known as copper-catalyzed azide-alkyne cycloaddition (CuAAC) reactions. However, click chemistry reactions between cyclooctyne or cyclooctyne derivatives and azides typically do not require the addition of a copper catalyst, and instead proceed via strain-promoted azide-alkyne cycloaddition (SPAAC) (Debets, M. F., et al., Bioconjugation with strained alkenes and alkynes. *Acc Chem Res,* 2011. 44(9): p. 805-15).

Site-specificity has become a key area of focus in the antibody-drug conjugate (ADC) field (Agarwal, P. and C. R. Bertozzi, Site-specific antibody-drug conjugates: the *nexus* of bioorthogonal chemistry, protein engineering, and drug development. *Bioconjug Chem,* 2015. 26(2): p. 176-92), as it has been demonstrated that both efficacy and safety of ADCs can be increased with site-specific methods as compared to random conjugation. It is thought that similar safety and efficacy benefits could be achieved for radioimmunoconjugates.

As indicated above, there remains a need in the art for efficient methods of producing stable radioimmunoconjugates with high specific activity and high yield.

BRIEF SUMMARY OF THE INVENTION

The invention satisfies this need by providing methods for using click chemistry to radiolabel polypeptides, such as antibodies. In a method of the invention, an azide-modified antibody and a radiocomplex comprising a radiometal ion associated with a chelating moiety comprising an alkyne group are used in a click chemistry reaction to produce stable radioimmunoconjugates having a low chelator:antibody ratio (CAR) and high radiochemical yields, while requiring reduced usage of the radioactive metal and only requiring metal-free conditions in the step used to produce the initial radiocomplex. Methods of the invention simplify previous methods for producing radioimmunoconjugates with increased safety, efficacy and uniformity.

In one general aspect, the invention relates to a method of labeling a polypeptide with a radiometal ion, the method comprising:
  a. providing a modified polypeptide comprising the polypeptide covalently linked to a first click reaction partner;
  b. providing a radiocomplex comprising the radiometal ion associated with a chelating moiety, wherein the chelating moiety comprises a chelant covalently linked to a second click reaction partner; and
  c. contacting the modified polypeptide with the radiocomplex under a condition to allow the first click reaction partner to react with the second click reaction partner thereby label the polypeptide with the radiometal ion.

In another general aspect, the invention relates to a pharmaceutical composition comprising a radiolabeled polypeptide prepared by a method of the invention and a pharmaceutically acceptable carrier.

In another general aspect, the invention relates to a method of treating a neoplastic disease or disorder in a subject in need thereof, comprising administering to the subject a pharmaceutical composition of the invention.

In another general aspect, the invention relates to a combination or kit comprising:
  a. a modified polypeptide comprising a polypeptide covalently linked to a first click reaction partner; and
  b. a radiocomplex comprising a radiometal ion associated with a chelating moiety, wherein the chelating moiety comprises a chelant covalently linked to a second click reaction partner;
  wherein the combination or kit is to be used for labeling the polypeptide with the radiometal ion.

In other general aspects, the invention relates to a therapeutic or diagnostic agent ("theranostic agent") comprising a radiolabeled polypeptide prepared by a method of the invention.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 3A shows the binding to the human prostate cancer cell line C4-2B (PSMA+, Transferrin receptor+) by a PSMA-binding antibody ("PSMB127") In-111 radioimmunoconjugate and a human transferrin In-111 radioconjugate according to embodiments of the application;

FIG. 3B shows the binding to the human epidermoid carcinoma cancer cell line A431 (EGFR+) by EGFR-binding antibodies cetuximab and panitumumab In-111 radioimmunoconjugates according to embodiments of the application, and the lack of binding of these conjugates to the control (EGFR−) human AML cell line MOLM-13;

FIG. 5A shows the tumor volume for each group; sizes were plotted until under half of the group remained;

FIG. 5B shows survival curves for control mAb groups; FIG. 5C shows survival curves for anti-PSMA mAb groups.

DETAILED DESCRIPTION OF THE INVENTION

Figure 1:
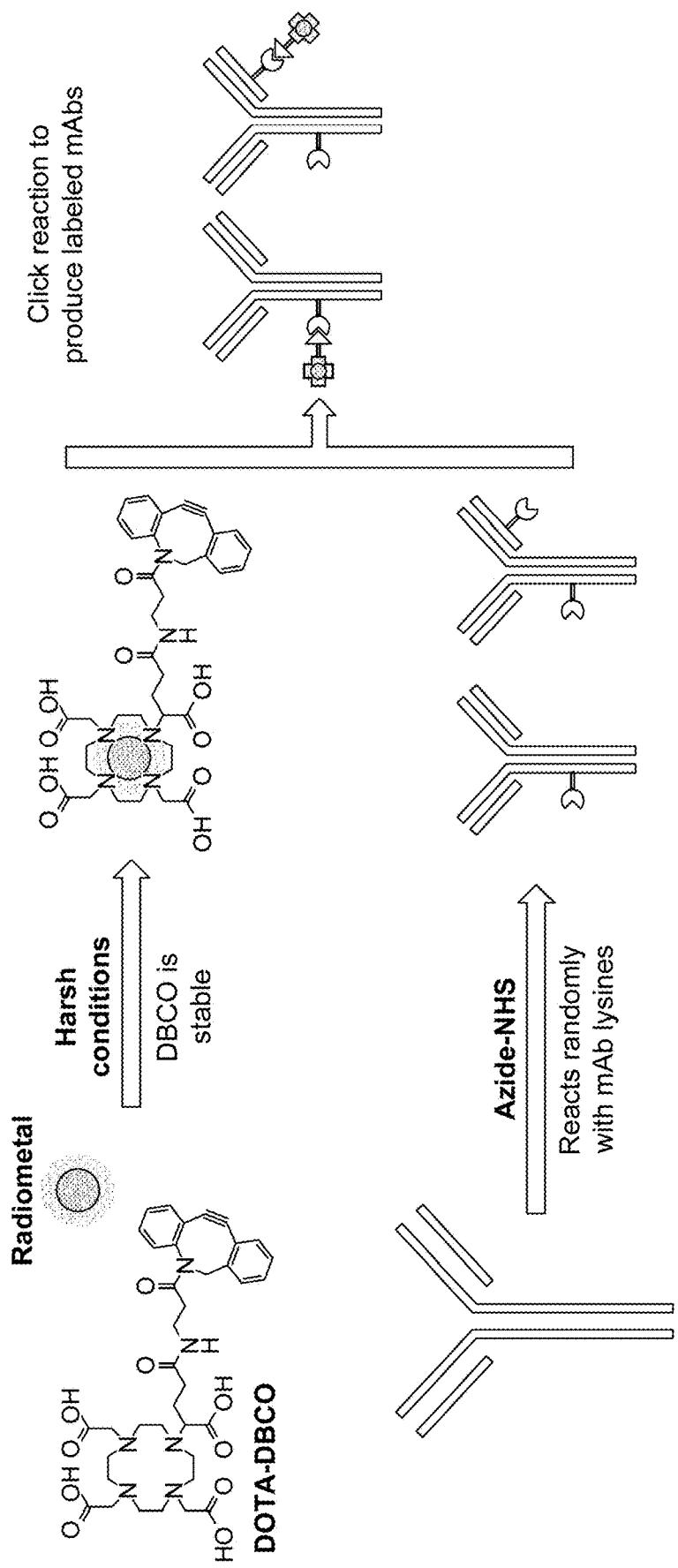
FIG. 1 shows a schematic of radiolabeling an antibody according to a method of the invention; random conjugation is shown in the figure, and a similar radiolabeling scheme is used when the azides are conjugated to the monoclonal antibody (mAb) site-specifically.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms cited herein have the meanings as set in the specification. All patents, published patent applications and publications cited herein are incorporated by reference as if set forth fully herein It must be noted that as used herein and in the appended claims, the singular forms "a," "an," and "the" include plural reference unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

In an attempt to help the reader of the application, the description has been separated into various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples.

Click Radiolabeling of Polypeptides

In contrast to known procedures, methods of the present invention provide for an improved method for the production of radioimmunoconjugates that are suitable, for example, for medicinal applications in subjects, e.g., humans, in need thereof. In particular, methods described herein address the major limitations of current methods by providing processes for both high yield chelation of metal ions, including but not limited to, $^{225}$Ac, $^{111}$In and $^{89}$Zr, and for low DAR. The invention allows for the production of a single batch of azide-labeled polypeptides, such as azide-mAb conjugate that can then be used for the production of a radiolabeled diagnostic (e.g., when labeled with $^{89}$Zr or $^{111}$In) or therapeutic (e.g., when labeled with $^{225}$Ac) purposes, in which the radiolabel is attached at the same site(s) within the batch of azide-labeled polypeptides, which can be obtained either by site-specific modification or by random azide conjugation. For example, in the case of random azide conjugation, samples of a batch of azide-labeled polypeptides comprising a single distribution of azide-modified sites can be radiolabeled for different purposes using click chemistry of the invention.

A method of the invention, which relies on click chemistry and is referred to as "click radiolabeling", involves (1) obtaining a modified polypeptide, such as an antibody, that includes a first click chemistry reaction partner, e.g. an azide moiety; (2) obtaining a radiocomplex comprising a radiometal ion, e.g., $^{225}$Ac, $^{111}$In or $^{89}$Zr, associated with a chelating moiety, wherein the chelating moiety comprises a chelant covalently liked to a second click chemistry reaction partner, e.g. an alkyne group, such as DOTA-dibenzocyclooctyne (DOTA-DBCO) or deferoxamine-DBCO (DFO-DBCO); and (3) conducting a reaction between the click chemistry reaction partners of the modified peptide and the radiocomplex, such as a strain-promoted alkyne-azide cycloaddition (SPAAC) between the azide moiety and the alkyne group.

A method of the invention allows chelation of the radioactive metal under low or high pH and/or high temperature conditions to maximize efficiency, which can be accomplished without the risk of inactivating the alkyne reaction partner. The efficient chelation and efficient SPAAC reaction between azido-mAb and the radiocomplex allows radioimmunoconjugates to be produced with high radiochemical yield even with low azide:mAb ratios. In a method of the invention, the only step in which trace metals must be excluded is the radiometal ion chelation to the chelating moiety; the antibody production, purification, and conjugation steps do not need to be conducted under metal free conditions.

As used herein, the term "click chemistry" refers to a chemical philosophy introduced by Sharpless, describing chemistry tailored to generate covalent bonds quickly and reliably by joining small units comprising reactive groups together (see Kolb, et al., supra). Click chemistry does not refer to a specific reaction, but to a concept including, but not limited to, reactions that mimic reactions found in nature. In some embodiments, click chemistry reactions are modular, wide in scope, give high chemical yields, generate inoffensive byproducts, are stereospecific, exhibit a large thermodynamic driving force to favor a reaction with a single reaction product, and/or can be carried out under physiological conditions. In some embodiments, a click chemistry reaction exhibits high atom economy, can be carried out under simple reaction conditions, uses readily available starting materials and reagents, uses no toxic solvents or uses a solvent that is benign or easily removed, such as water, and/or provides simple product isolation by non-chromatographic methods, such as crystallization or distillation. In certain embodiments, the click chemistry reaction is a Huisgen cycloaddition or the 1,3-dipolar cycloaddition between an azide (—N3) and an alkyne, or an alkyne moiety, to form a 1,2,4-triazole linker.

In a general aspect, the invention relates to a method of labeling a polypeptide, an aptamer, or a small molecule ligand with a radiometal ion, the method comprising:
a. providing a modified polypeptide comprising the polypeptide covalently linked to a first click reaction partner;
b. providing a radiocomplex comprising the radiometal ion associated with a chelating moiety, wherein the chelating moiety comprises a chelant covalently linked to a second click reaction partner; and
c. contacting the modified polypeptide with the radiocomplex under a condition to allow the first click reaction partner to react with the second click reaction partner to thereby label the polypeptide with the radiometal ion.

As used herein, the term "polypeptide" refers to a polymer composed of amino acid residues, related naturally occurring structural variants, and synthetic non-naturally occurring analogs thereof linked via peptide bonds. The term refers to a polypeptide of any size, structure, or function. Typically, a polypeptide is at least three amino acids long. A polypeptide can be naturally occurring, recombinant, or synthetic, or any combination thereof. Synthetic polypeptides can be synthesized, for example, using an automated polypeptide synthesizer. According to preferred embodiments, the polypeptide is an antibody, preferably a monoclonal antibody, or a fragment thereof, such as an antigen-binding fragment thereof. According to preferred embodiments, the antibody or fragment thereof is specific for a cancer antigen. According to other embodiments, the polypeptide is an engineered domain or a scaffold protein.

As used herein, the term "antibody" or "immunoglobulin" is used in a broad sense and includes immunoglobulin or antibody molecules including polyclonal antibodies, monoclonal antibodies including murine, human, human-adapted, humanized and chimeric monoclonal antibodies, and antigen-binding fragments thereof.

In general, antibodies are proteins or peptide chains that exhibit binding specificity to a specific antigen, referred to herein as a "target". Antibody structures are well known. Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of any vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from mouse antibodies or human antibodies. Each of the four IgG subclasses has different biological functions known as effector functions. These effector functions are generally mediated through interaction with the Fc receptor (FcγR) or by binding C1q and fixing complement. Binding to FcγR can lead to antibody dependent cell mediated cytolysis, whereas binding to complement factors can lead to complement mediated cell lysis. An antibody useful for the invention can have no or minimal effector function, but retain its ability to bind FcRn.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "scaffold" or "scaffold protein" refers to any protein that has a target binding domain and that can bind to a target. A scaffold contains a "framework", which is largely structural, and a "binding domain" which makes contact with the target and provides for specific binding. The binding domain of a scaffold need not be defined by one contiguous sequence of the scaffold. In certain cases, a scaffold may be part of larger binding protein, which, itself, may be part of a multimeric binding protein that contains multiple scaffolds. Certain binding proteins may be bi- or multi-specific in that they can bind to two or more different epitopes. A scaffold can be derived from a single chain antibody, or a scaffold may be not antibody-derived.

Polypeptides of the invention can be covalently linked to a first click reaction partner using any method for chemical or enzymatic modification of a polypeptide known to those skilled in the art in view of the present disclosure. Amine-reactive groups that react with primary amines that exist at the N-terminus of each polypeptide chain and in the side-chain of lysine residues can be used in methods for random modification of polypeptides. Examples of amine-reactive groups suitable for use in the invention include, but are not limited to, N-hydroxy succinimide (NHS), substituted NHS, such as sulfo-NHS, isothiocyanate, and tetra- and per-fluoro phenyl ester. Thiol-reactive groups that react with thiols, or sulfhydryls, that exist in the side-chain of cysteine residues can be used in methods for random modification of polypeptides. Examples of thiol-reactive groups suitable for use in the invention include, but are not limited to, maleimide, haloacetyl and phenyloxadiazole sulfone. According to preferred embodiments, a modified polypeptide is obtained by reacting a side chain, preferably the amino side chain of a lysine, with an electrophile covalently linked to the first click reaction partner (e.g. NHS-azide).

A method of the invention further allows the production of site-specific radiolabeled polypeptides. The click radiolabeling method of the invention facilitates site-specific production of radioimmunoconjugates by taking advantage of established methods to install azide groups site-specifically on antibodies (Li, X., et al. Preparation of well-defined antibody-drug conjugates through glycan remodeling and strain-promoted azide-alkyne cycloadditions. *Angew Chem Int Ed Engl*, 2014. 53(28): p. 7179-82; Xiao, H., et al., Genetic incorporation of multiple unnatural amino acids into proteins in mammalian cells. *Angew Chem Int Ed Engl*, 2013. 52(52): p. 14080-3). Methods of attaching molecules to proteins or antibodies in a site-specific manner are known in the art, and any method of site-specifically labeling an antibody known to those skilled in the art can be used in the invention in view of the present disclosure. Examples of methods to site-specifically modify antibodies suitable for use in the invention include, but are not limited to, incorporation of engineered cysteine residues (e.g., THIO-MAB®), use of non-natural amino acids or glycans (e.g., seleno cysteine, p-AcPhe, formylglycine generating enzyme (FGE, SMARTag®), etc.), and enzymatic methods (e.g., use of glycotransferase, endoglycosidase, microbial or bacterial transglutaminase (MTG or BTG), sortase A, etc.). According to preferred embodiments, the modified polypeptide is an antibody or antigen binding fragment thereof that is obtained by trimming the antibody or antigen binding fragment thereof with a bacterial endoglycosidase specific for the ß-1,4 linkage between a core GlcNac residue in a Fc-glycosylation site of the antibody, such as GlycINATOR® (Genovis), which leaves the inner most GlcNAc intact on the Fc, allowing for the site-specific incorporation of azido sugars at that site. The trimmed antibody or antigen binding fragment thereof can then be reacted with an azide-labeled sugar, such as UDP-N-azidoacetylgalactosamine (UDP-Gal-Naz) or UDP-6-azido 6-deoxy GalNAc, in the presence of a sugar transferase, such as GalT galactosyltransferase or GalNAc transferase, to thereby obtain the modified antibody or antigen binding fragment thereof. According to other preferred embodiments, modified polypeptide is an antibody or antigen binding fragment thereof that is obtained by deglycosylating the antibody or antigen binding fragment thereof with an amidase. The resulting deglycosylated antibody or antigen binding fragment thereof can then be reacted with an azido amine, preferably 3-azido propylamine, 6-azido hexylamine, or any azido-linker-amine or any azido-alkyl-amine, such as an azido-polyethylene glycol (PEG)-amine, for example, O-(2-Aminoethyl)-O'-(2-azido-ethyl)tetraethylene glycol, O-(2-Aminoethyl)-O'-(2-azido-ethyl)pentaethylene glycol, O-(2-Aminoethyl)-O'-(2-azido-ethyl)triethylene glycol, etc., or in the presence of a microbial transglutaminase to thereby obtain the modified antibody or antigen binding fragment thereof.

As used herein, the term "aptamer" refers to a single-stranded oligonucleotide (single-stranded DNA or RNA molecule) that can bind specifically to its target with high affinity. The aptamer can be used as a molecule targeting various organic and inorganic materials.

As used herein, the term "small molecule ligand" refers to a low molecular weight organic compound. Small molecule ligands, as used herein, can refer to compounds that have a size of less than about 1000 daltons, and can be synthesized in the laboratory or found in nature.

As used herein, the term "click reaction partner" or "click chemistry handle" refers to a reactant or a reactive group that can partake in a click chemistry reaction. A click reaction partner can be a moiety that is rarely found in naturally-occurring biomolecules and is chemically inert towards biomolecules, but, e.g., when reacted with an azide-reactive or alkyne-reactive group, the reaction can take place efficiently under biologically relevant conditions, for example in cell culture conditions, such as in the absence of excess heat or harsh reactants. In general, click chemistry reactions require at least two molecules comprising click reaction partners that can react with each other. Such click reaction partners that are reactive with each other are sometimes referred to herein as click chemistry handle pairs, or click chemistry pairs. In some embodiments, the click reaction partners are an azide and a strained alkyne, e.g. a cyclooctyne, or any other alkyne. In other embodiments, the click reaction partners are reactive dienes and suitable tetrazine dienophiles. For example, trans-cyclooctene, norbornene, or biscyclononene can be paired with a suitable tetrazine dienophile as a click reaction pair. In yet other embodiments, tetrazoles can act as latent sources of nitrile imines, which can pair with unactivated alkenes in the presence of ultra-violet light to create a click reaction pair, termed a "photo-click" reaction pair. In other embodiments, the click reaction partners are a cysteine and a maleimide. For example the cysteine from a peptide (e.g., GGGC) can be reacted with a maleimide that is associated with a chelating agent (e.g., NOTA). Other suitable click chemistry handles are known to those of skill in the art (see, e.g., Spicer et al., Selective chemical protein modification. *Nature Communications*. 2014; 5: p. 4740). In other embodiments, the click reaction partners are Staudinger ligation components, such as phosphine and azide. In other embodiments, the click reaction partners are Diels-Alder reaction components, such as dienes, such as tetrazine, and alkenes, such as trans-cyclooctene (TCO) or norbornene. Exemplary click reaction partners are described in US20130266512 and in WO2015073746, the relevant description on click reaction partners in both of which are incorporated by reference herein. According to preferred embodiments, one of the first and second click reaction partners comprises an alkyne group, and the other click reaction partner comprises an azide. According to other preferred embodiments, one of the first and second click reaction partners comprises an alkene group, and the other click reaction partner comprises a diene.

As used herein, the term "alkyne", "alkyne group" or "alkyne moiety" refers to a functional group comprising a carbon-carbon triple bond. Alkyne moieties include terminal alkynes and cyclic alkynes, preferably terminal alkynes and cyclic alkynes that are reactive with azide groups. A terminal alkyne has at least one hydrogen atom bonded to a triply bonded carbon atom. A cyclic alkyne is a cycloalkyl ring comprising one or more triple bonds. Examples of cyclic alkynes include, but are not limited to, cyclooctyne and cyclooctyne derivatives, such as bicyclononyne (BCN), difluorinated cyclooctyne (DIFO), dibenzocyclooctyne (DIBO), keto-DIBO, biarylazacyclooctynone (BARAC), dibenzoazacyclooctyne (DIBAC), dimethoxyazacyclooctyne (DIMAC), dibenzyocyclooctyne (DBCO), difluorobenzocyclooctyne (DIFBO), monobenzocyclooctyne (MOBO), and tetramethoxy DIBO (TMDIBO). According to preferred embodiments, one of the first and second click reaction partners comprises a cyclic alkyne, preferably DBCO. According to preferred embodiments, the other click reaction partner comprises an azide, preferably NHS-azide.

As used herein, the term "diene" refers to a compound having two carbon-to-carbon double bonds where these double bonds are conjugated in the 1,3-position. The double bonds of the diene can be either cis or trans. Examples of dienes include, but are not limited to, a tetrazine or a tetrazole group.

As used herein, the term "alkene", "alkene group" or "alkene moiety" refers to an unsaturated hydrocarbon molecule that includes a carbon-carbon double bond. According to particular embodiments, an alkene can include from 2 to 100 carbon atoms. Examples of alkenes include, but are not limited to, norbornene and trans-cyclooctene (TCO). According to other preferred embodiments, one of the first and second click reaction partners comprises an alkene group, preferably norbornene or TCO. According to preferred embodiments, the other click reaction partner comprises a diene, preferably a tetrazine or tetrazole group.

As used herein, the term "covalently linked" means that the polypeptide is attached to the first click reaction partner via at least one covalent linkage, and that the chelant is attached to the second click reaction partner via at least one covalent linkage. The linkage can be direct, i.e. without a linker, or indirect, i.e. via a linker.

As used herein, the term "linker" refers to a chemical moiety that joins a polypeptide or a chelant to a click reaction partner. Any suitable linker known to those skilled in the art in view of the present disclosure can be used in the invention. The linkers can be, for example, a single covalent bond, a substituted or unsubstituted alkyl, a substituted or unsubstituted heteroalkyl moiety, a polyethylene glycol (PEG) linker, a peptide linker, a sugar-based linker, or a cleavable linker, such as a disulfide linkage or a protease cleavage site such as valine-citrulline-PAB.

As used herein, the term "radiometal ion" or "radioactive metal ion" refers to one or more isotopes of the elements that emit particles and/or photons. Any radioactive metal known to those skilled in the art in view of the present disclosure can be used in the invention. Examples of radioactive metals suitable for use in the invention include, but are not limited to, $^{32}$P, $^{47}$Sc, $^{62}$Cu, $^{64}$Cu, $^{67}$Cu, $^{67}$Ga, $^{68}$Ga, $^{77}$As, $^{86}$Y, $^{89}$Zr, $^{89}$Sr, $^{90}$Y, $^{99}$Tc, $^{105}$Rh, $^{109}$Pd, $^{111}$Ag, $^{111}$In, $^{117}$Sn, $^{131}$I, $^{153}$Sm, $^{159}$Gd, $^{165}$Dy, $^{166}$Ho, $^{169}$Er, $^{177}$Lu, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{225}$Ac, $^{227}$Th, and $^{255}$Fm. As used herein, the term "diagnostic emitter" refers to a radiometal ion that is useful in diagnostic or imaging applications. Examples of diagnostic emitters include, but are not limited to gamma emitters, such as $^{62}$Cu, $^{64}$Cu, $^{67}$Ga, $^{68}$Ga, $^{86}$Y, $^{89}$Zr, and $^{111}$In. As used herein, the term "therapeutic emitter" refers to a radiometal ion that is useful in therapeutic applications. Examples of therapeutic emitters include, but are not limited to, beta or alpha emitters, such as thorium, radium, $^{32}$P, $^{47}$Sc, $^{67}$Cu, $^{77}$As, $^{89}$Sr, $^{90}$Y, $^{99}$Tc, $^{105}$Rh, $^{109}$Pd, $^{111}$Ag, $^{131}$I, $^{153}$Sm, $^{159}$Gd, $^{165}$Dy, $^{166}$Ho, $^{169}$Er, $^{177}$Lu, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{225}$Ac, $^{255}$Fm and $^{227}$Th. According to preferred embodiments, the radiometal ion is $^{225}$Ac. According to other embodiments, the polypeptide can be labeled with non-metal radiolabels for use in pre-targeting or theranostic applications. Examples of non-metal radiolabels suitable for use in the invention include, but are not limited to, $^{125}$I and $^{18}$F.

Radiocomplexes described herein comprise a radiometal ion associated with a chelating moiety. According to embodiments of the invention, the chelating moiety comprises a chelant covalently linked to a click reaction partner, and is sometimes referred to herein as a "bifunctional chelator."

As used herein, the term "chelant" or "chelator" refers to a chemical compound to which a radiometal, such as $^{225}$Ac, or metal can be chelated via coordinate bonding. Any chelant known to those skilled in the art in view of the present disclosure can be used in the invention. In an embodiment, the chelant comprises a macrocycle. Examples of chelants comprising a macrocycle suitable for use in the invention include, but are not limited to, deferoxamine (DFO), ethylenediaminetetraacetic acid (EDTA), and diethylenetriaminepentaacetic acid (DTPA). In another embodiment, the chelant comprises an open chain ligand. Examples of chelants comprising an open chain ligand suitable for use in the invention include, but are not limited to, 1,4,7,10-tetraazacyclododecane-N,N',N",N"'-tetraacetic acid (DOTA), 1,4,7,10,13,16-hexaazacyclohexadecane-N,N',N", N"',N"",N""'-hexaacetic acid (HEHA), 1,4,7,10,13-pentaazacyclopentanadecane-N,N',N",N"', N""-pentaacetic acid (PEPA), Macropa (Thiele et al., An Eighteen-Membered Macrocyclic Ligand for Actinium-225 Targeted Alpha Therapy. Angew Chem Int Ed Engl. 2017 Nov. 13; 56(46): p. 14712-14717), 1,4,8,11-tetraazacyclotetradecane-1,4,8, 11-tetraacetic acid (TETA), 1,4,7,10-tetraazacyclododecane-1,4,7,10-tetrapropionic acid (DOTPA), 1,4,8,11-tetraazacyclotetradecane-1,4,8,11-tetrapropionic acid (TETPA), and 1,4,7,10-tetraazacyclododecane-1,4,7,10-tetramethylenephosphonic acid (DOTMP). According to preferred embodiments, the chelant comprises a structure of formula (I):

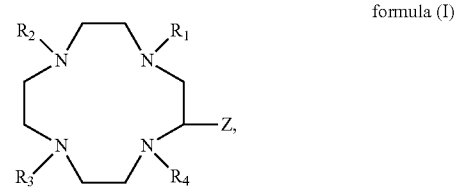

formula (I)

wherein each of $R_1$, $R_2$, $R_3$ and $R_4$ is independently CHQCO$_2$X, wherein Q is independently hydrogen, $C_1$-$C_4$ alkyl or ($C_1$-$C_2$ alkyl) phenyl, and X is independently hydrogen, benzyl, $C_1$-$C_4$ alkyl; and Z is (CH$_2$)$_n$Y, wherein n is 1-10, and Y is an electrophilic or nucleophilic moiety covalently linked to the second click reaction partner;

alternatively, Z is hydrogen; and each of $R_1$, $R_2$, $R_3$ and $R_4$ is independently CHQCO$_2$X, wherein Q is independently hydrogen, $C_1$-$C_4$ alkyl or ($C_1$-$C_2$ alkyl) phenyl, and X is independently hydrogen, benzyl, $C_1$-$C_4$ alkyl, or an electrophilic or nucleophilic moiety covalently linked to the second click reaction partner.

According to preferred embodiments, the chelating moiety comprises the structure of formula (II):

formula (II)

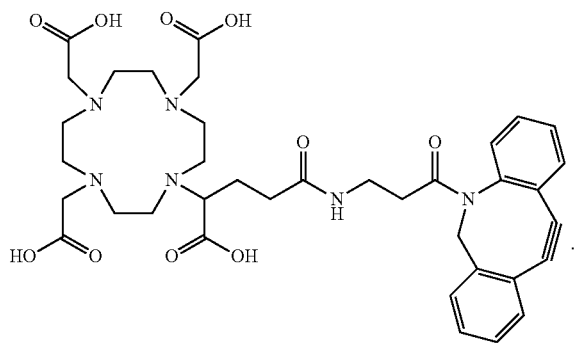

According to preferred embodiments, the chelating moiety comprises the structure of formula (III):

formula (III)

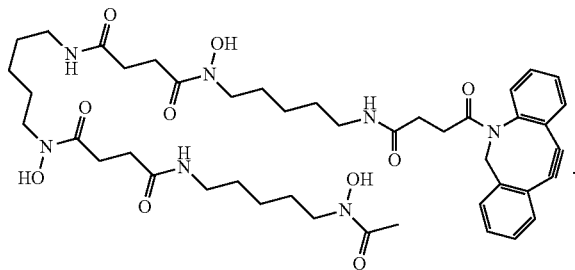

In an embodiment, the invention relates to a method of labeling a polypeptide with two or more radiometal ions using a method of the invention. For example, a method of dually labeling a polypeptide with two radiometal ions comprises:
  a. providing a modified polypeptide comprising the polypeptide covalently linked to a first click reaction partner and a second click reaction partner;
  b. providing a first radiocomplex comprising the first radiometal ion associated with a chelating moiety, wherein the chelating moiety comprises a chelant covalently linked to a third click reaction partner; and
  c. providing a second radiocomplex comprising the second radiometal ion associated with a chelating moiety, wherein the chelating moiety comprises a chelant covalently linked to a fourth click reaction partner; and
  d. contacting the modified polypeptide with the first and second radiocomplexes under a condition to allow the first click reaction partner to react with the third click reaction partner, and the second click reaction partner to react with the fourth click reaction partner, to thereby label the polypeptide with the first and second radiometal ions.

According to preferred embodiments, one of the first and second click reaction partners comprises an alkyne group, and the other of the first and second click reaction partner comprises an azide, and wherein one of the third and fourth click reaction partners comprises an alkene group, and the other of the third and fourth click reaction partner comprises a diene.

According to preferred embodiments, the first or second radiometal ion is a diagnostic emitter, and the other is a therapeutic emitter. According to other preferred embodiments, both the first and second radiometal ions are therapeutic emitters.

Conditions for carrying out click chemistry reactions are known in the art, and any conditions for carrying out click chemistry reactions known to those skilled in the art in view of the present disclosure can be used in the invention. Examples of conditions include, but are not limited to, incubating the modified polypeptide and the radiocomplex at a ratio of 1:1 to 1000:1 at a pH of 4 to 10 and a temperature of 20° C. to 70° C.

Products of click radiolabeling methods of the invention can be analyzed using methods known to those skilled in the art in view of the present disclosure. For example, LC/MS analysis can be used to determine the ratio of the chelator to the labeled polypeptide; analytical size-exclusion chromatography can be used to determine the oligomeric state of the polypeptides and polypeptide conjugates; radiochemical yield can be determined by instant thin layer chromatography (e.g. iTLC-SG), and radiochemical purity can be determined by size-exclusion HPLC. Exemplary methods are described herein, e.g., in the Examples below.

Pharmaceutical Compositions and Methods of Treatment

The click radiolabeling method of the invention can be modified into a pre-targeting approach (Kraeber-Bodere, F., et al., A pretargeting system for tumor PET imaging and radioimmunotherapy. *Front Pharmacol*, 2015. 6: p. 54). First, the azido-mAb is dosed, binds to target cells, and is allowed to clear from circulation over time or removed with a clearing agent. Subsequently, the radiocomplex is administered and undergoes the SPAAC reaction with azido-mAbs bound at the target site, while the remaining unbound radiocomplex clears rapidly from circulation (Deal, K. A., et al., Improved in vivo stability of actinium-225 macrocyclic complexes. *J Med Chem*, 1999. 42(15): p. 2988-92). This pre-targeting technique provides a method of enhancing radiometal ion localization at a target site in a subject Accordingly, in another general aspect, the invention relates to a pharmaceutical composition comprising a radiolabeled polypeptide prepared by a method of the invention and a pharmaceutically acceptable carrier.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody-based, or a radiocomplex-based pharmaceutical composition can be used in the invention.

According to particular embodiments, the compositions described herein are formulated to be suitable for the intended route of administration to a subject. For example, the compositions described herein can be formulated to be suitable for intravenous, subcutaneous, intramuscular or intratumoral administration.

According to particular embodiments, the modified polypeptide and the radiocomplex can be administered in the same or different compositions.

In another general aspect, the invention relates to a method of treating a neoplastic disease or disorder in a subject in need thereof, comprising administering to the subject the pharmaceutical composition of the invention.

According to particular embodiments, a method of the invention comprises administering a therapeutically effective dose of a pharmaceutical composition of the invention, wherein the composition comprises a radiolabeled polypeptide for targeting cells associated with the neoplastic disease or disorder such that, upon targeting, alpha particles from the $^5$Ac and daughters thereof are delivered to the targeted cells and cause a cytotoxic effect thereto, thereby treating the neoplastic disease or disorder.

According to particular embodiments, therapeutically effective amounts of the modified polypeptide and the radiocomplex are administered in different compositions.

As used herein, the term "therapeutically effective amount" refers to an amount of an active ingredient or component that elicits the desired biological or medicinal response in a subject. A therapeutically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

As used herein, the terms "treat," "treating," and "treatment" are all intended to refer to an amelioration or reversal of at least one measurable physical parameter related to a disease, disorder, or condition in which administration of a radioactive metal ion would be beneficial, such as a neoplastic disease or disorder, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition in which administration of a radioactive metal ion would be beneficial, such as a neoplastic disease or disorder. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

Examples of neoplastic diseases or disorders include, but are not limited to, a disseminated cancer, a solid tumor cancer, a hypertrophy, a coronary disease, or a vascular occlusive disease, a disease or disorder associated with an infected cell, a microbe or a virus, or a disease or disorder associated with an inflammatory cell, such as rheumatoid arthritis (RA).

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig, marmoset or mouse) or a primate (e.g., a monkey, chimpanzee, or human). In particular embodiments, the subject is a human.

Any dosing schedule of the modified polypeptide and the radiocomplex can be used in view of the present disclosure. In general, when the modified polypeptide and the radiocomplex are administered in different compositions, the radiocomplex can be administered any time after the modified antibody is administered.

According to particular embodiments, compositions used in the treatment of a neoplastic disease or disorder can be used in combination with other agents that are effective for treatment of related neoplastic diseases or disorders.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a theranostic agent comprising a radiolabeled antibody prepared by a method of the invention and a pharmaceutically acceptable carrier, wherein the immunological properties of the radiolabeled antibody are preserved.

As used herein, the term "theranostic" refers to the ability to provide either of diagnostic and therapeutic functions. In one embodiment, a theranostic agent provides both diagnostic and therapeutic functions. In another embodiment, a theranostic agent is an active pharmaceutical agent without diagnostic function. In yet another embodiment, a theranostic agent is an agent useful for diagnosis but having no therapeutic function.

According to preferred embodiments, the radiometal ion is a diagnostic emitter, preferably $^{89}$Zr. According to other preferred embodiments, the radiometal ion is a therapeutic emitter, preferably $^{225}$Ac. According to preferred embodiments, the theranostic agent is used to provide both diagnostic and therapeutic functions to a subject in need thereof.

Combinations and Kits

Provided herein is a combination comprising:
a. a modified polypeptide comprising a polypeptide covalently linked to a first click reaction partner; and
b. a radiocomplex comprising a radiometal ion associated with a chelating moiety, wherein the chelating moiety comprises a chelant covalently linked to a second click reaction partner;
wherein the combination is to be used for labeling the polypeptide with the radiometal ion.

According to particular embodiments, a combination of the invention is a reaction mixture used to label the polypeptide with the radiometal ion. According to other embodiments, the combination is a pack or kit used to produce a radiolabeled polypeptide, in vitro or in vivo. Optionally associated with the combination can be a notice or instructions in the form prescribed by a governmental agency regulating the manufacture, use or sale of pharmaceuticals or biological products, which notice reflects approval by the agency of manufacture, use or sale for human administration. The combinations encompassed herein can be used in the above methods of labeling a polypeptide with a radiometal ion, or of treating a neoplastic disease or disorder in a subject in need thereof.

EMBODIMENTS

The invention provides also the following non-limiting embodiments.

Embodiment 1 is a method of labeling a polypeptide with a radiometal ion, the method comprising:
 a. providing a modified polypeptide comprising the polypeptide covalently linked to a first click reaction partner;
 b. providing a radiocomplex comprising the radiometal ion associated with a chelating moiety, wherein the chelating moiety comprises a chelant covalently linked to a second click reaction partner; and
 c. contacting the modified polypeptide with the radiocomplex under a condition to allow the first click reaction partner to react with the second click reaction partner to thereby label the polypeptide with the radiometal ion.

Embodiment 1a is the method of Embodiment 1, wherein the chelant comprises a macrocycle.

Embodiment 1b is the method of Embodiment 1, wherein the chelant comprises an open chain ligand.

Embodiment 2 is the method of Embodiment 1, wherein one of the first and second click reaction partners comprises an alkyne group, and the other click reaction partner comprises an azide.

Embodiment 3 is the method of Embodiment 2, wherein the first click reaction partner comprises an azide group and the second click reaction partner comprises an alkyne group.

Embodiment 3a is the method of Embodiment 2 or 3, wherein the alkyne group comprises a terminal alkyne.

Embodiment 3b is the method of Embodiment 2 or 3, wherein the alkyne group comprises a cyclic alkynes, preferably a cyclooctyne or cyclooctyne derivative.

Embodiment 3c is the method of Embodiment 3b, wherein the alkyne group comprises bicyclononyne (BCN).

Embodiment 3d is the method of Embodiment 3b, wherein the alkyne group comprises difluorinated cyclooctyne (DIFO).

Embodiment 3e is the method of Embodiment 3b, wherein the alkyne group comprises dibenzocyclooctyne (DIBO).

Embodiment 3f is the method of Embodiment 3b, wherein the alkyne group comprises biarylazacyclooctynone (BARAC).

Embodiment 3g is the method of Embodiment 3b, wherein the alkyne group comprises dibenzoazacyclooctyne (DIBAC).

Embodiment 3h is the method of Embodiment 3b, wherein the alkyne group comprises dimethoxyazacyclooctyne (DIMAC).

Embodiment 3i is the method of Embodiment 3b, wherein the alkyne group comprises dibenzyocyclooctyne (DBCO).

Embodiment 3j is the method of Embodiment 3b, wherein the alkyne group comprises difluorobenzocyclooctyne (DIFBO).

Embodiment 3k is the method of Embodiment 3b, wherein the alkyne group comprises monobenzocyclooctyne (MOBO).

Embodiment 3l is the method of Embodiment 3b, wherein the alkyne group comprises tetramethoxy DIBO (TMDIBO).

Embodiment 3m is the method of any one of Embodiments 2 to 3l, wherein the azide group comprises NHS-azide.

Embodiment 4 is the method of Embodiment 1, wherein one of the first and second click reaction partners comprises an alkene group, and the other click reaction partner comprises a diene.

Embodiment 4a is the method of Embodiment 4, wherein the diene comprises a tetrazine or tetrazole group.

Embodiment 4b is the method of Embodiment 4 or 4a, wherein the alkene group comprises norbornene.

Embodiment 4c is the method of Embodiment 4 or 4a, wherein the alkene group comprises trans-cyclooctene (TCO).

Embodiment 5 is the method of any one of Embodiments 1 to 4c, wherein the polypeptide is an antibody or an antigen binding fragment thereof.

Embodiment 6 is the method of Embodiment 5, wherein the antibody is a monoclonal antibody, or an antigen binding fragment thereof.

Embodiment 6a is the method of any one of Embodiments 1 to 6, wherein the modified polypeptide is obtained by randomly conjugating one or more azide groups to the polypeptide.

Embodiment 6b is the method of any one of Embodiments 1 to 6, wherein the modified polypeptide is a modified antibody or antigen binding fragment thereof obtained by site specific incorporation of the first click reaction partner.

Embodiment 6c is the method of Embodiment 6b, wherein the modified antibody or antigen binding fragment thereof is obtained by trimming the antibody or antigen binding fragment thereof with a bacterial endoglycosidase specific for the β-1,4 linkage between the core GlcNac residue(s) in the Fc-glycosylation site(s) of the antibody to obtain a trimmed antibody or antigen binding fragment thereof, and reacting the trimmed antibody or antigen binding fragment thereof with an azide sugar, preferably UDP-GalNaz azido sugar substrate, in the presence of a sugar transferase, preferably GalT galactosyltransferase.

Embodiment 6d is the method of Embodiment 6b, wherein the modified antibody or antigen binding fragment thereof is obtained by deglycosylating the antibody or antigen binding fragment thereof with an amidase to obtain a deglycosylated antibody or antigen binding fragment thereof, and reacting the deglycosylated antibody or antigen binding fragment thereof with an azido amine, preferably 3-azido propylamine, in the presence of a microbial transglutaminase.

Embodiment 6e is the method of any one of Embodiments 6 to 6d, wherein the antibody is an antibody that binds to human prostate-specific membrane antigen (PSMA) or an antigen binding fragment thereof, preferably the antibody comprises a HC CDR1 sequence of SEQ ID NO: 3, a HC CDR2 sequence of SEQ ID NO: 4, a HC CDR3 sequence of SEQ ID NO: 5, a light chain (LC) CDR1 sequence of SEQ ID NO: 6, a LC CDR2 sequence of SEQ ID NO: 7, and a LC CDR3 sequence of SEQ ID NO: 8.

Embodiment 6f is the method of Embodiment 6e, wherein the antibody comprises a HC sequence of SEQ ID NO: 9 and a LC sequence of SEQ ID NO: 10.

Embodiment 7 is the method of any one of Embodiments 1 to 6d, wherein the radiometal ion is $^{32}$P, $^{47}$Sc, $^{67}$Cu, $^{77}$As, $^{89}$Sr, $^{90}$Y, $^{99}$Tc, $^{105}$Rh, $^{109}$Pd, $^{111}$Ag, $^{131}$I, $^{153}$Sm, $^{159}$Gd, $^{165}$Dy, $^{166}$Ho, $^{169}$Er, $^{177}$Lu, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{225}$Ac, $^{255}$Fm, $^{227}$Th, $^{62}$Cu, $^{64}$Cu, $^{67}$Ga, $^{68}$Ga, $^{86}$Y, $^{89}$Zr, or $^{111}$In.

Embodiment 7a is the method of any one of Embodiments 1 to 6d, wherein the radiometal ion is $^{225}$Ac.

Embodiment 7b is the method of any one of Embodiments 1 to 6d, wherein the radiometal ion is $^{111}$In.

Embodiment 7c is the method of any one of Embodiments 1 to 6d, wherein the radiometal ion is $^{89}$Zr.

Embodiment 8 is the method of any one of Embodiments 1 to 7c, wherein the chelating moiety is covalently linked to the second click reaction partner via a linker.

Embodiment 9 is the method of any one of Embodiments 1 to 8, further comprising reacting an electrophile on a side chain, preferably the amino side chain of a lysine on or introduced to the polypeptide, with a sulfhydryl group covalently linked to the first click reaction partner to obtain the modified polypeptide, preferably NHS-azide.

Embodiment 10 is a method of any one of Embodiments 1 to 9, wherein the modified polypeptide comprises the polypeptide covalently linked, directly or via a linker, to an azide, tetrazine or tetrazole group.

Embodiment 11 is the method of any one of Embodiments 1 to 10, wherein the chelant comprises a macrocycle, preferably a structure of formula (I):

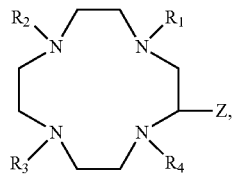

formula (I)

wherein each of $R_1$, $R_2$, $R_3$ and $R_4$ is independently CHQCO$_2$X, wherein Q is independently hydrogen, $C_1$-$C_4$ alkyl or ($C_1$-$C_2$ alkyl) phenyl, and X is independently hydrogen, benzyl, $C_1$-$C_4$ alkyl; and Z is (CH$_2$)$_n$Y, wherein n is 1-10, and Y is an electrophilic or nucleophilic moiety covalently linked to the second click reaction partner;

alternatively, Z is hydrogen; and each of $R_1$, $R_2$, $R_3$ and $R_4$ is independently CHQCO$_2$X, wherein Q is independently hydrogen, $C_1$-$C_4$ alkyl or ($C_1$-$C_2$ alkyl) phenyl, and X is independently hydrogen, benzyl, $C_1$-$C_4$ alkyl, or an electrophilic or nucleophilic moiety covalently linked to the second click reaction partner.

Embodiment 12 is the method of any one of Embodiments 1 to 11, wherein the chelating moiety comprises the structure of formula (II):

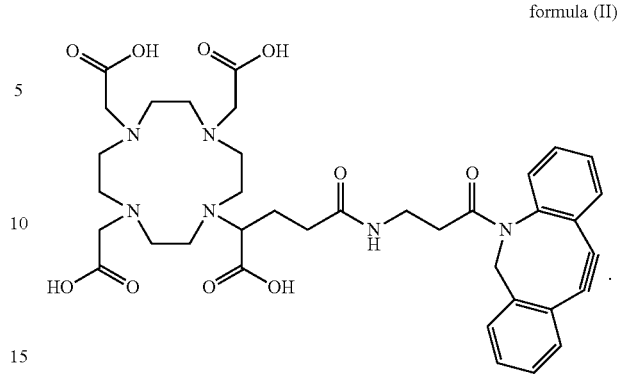

formula (II)

Embodiment 12a is the method of any one of Embodiments 1 to 11, wherein the chelating moiety comprises a chelant having an open chain ligand, preferably the chelating moiety having a structure of formula (III):

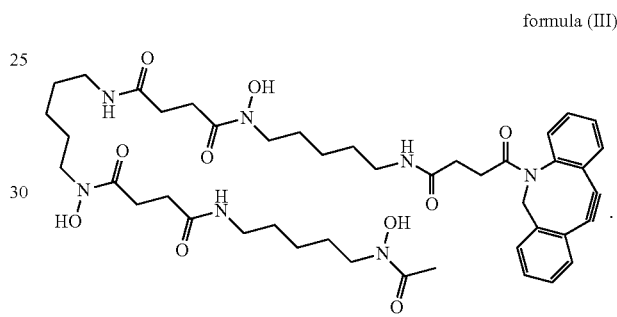

formula (III)

Embodiment 12b is the method of any one of Embodiments 1 to 10, wherein the chelating moiety comprises a chelant selected from the group consisting of 1,4,7,10-tetraazacyclododecane-N,N',N",N'''-tetraacetic acid (DOTA), deferoxamine (DFO), 1,4,7,10,13,16-hexaazacyclohexadecane-N,N',N",N''',N'''',N'''''-hexaacetic acid (HEHA), 1,4,7,10,13-pentaazacyclopentanadecane-N,N', N",N''', N''''-pentaacetic acid (PEPA), ethylenediaminetetraacetic acid (EDTA), diethylenetriaminepentaacetic acid (DTPA) Macropa (Thiele et al., An Eighteen-Membered Macrocyclic Ligand for Actinium-225 Targeted Alpha Therapy. Angew Chem Int Ed Engl. 2017 Nov. 13; 56(46): p. 14712-14717), 1,4,8,11-tetraazacyclotetradecane-1,4,8, 11-tetraacetic acid (TETA), 1,4,7,10-tetraazacyclododecane-1,4,7,10-tetrapropionic acid (DOTPA), 1,4,8,11-tetraazacyclotetradecane-1,4,8,11-tetrapropionic acid (TETPA), and 1,4,7,10-tetraazacyclododecane-1,4,7,10-tetramethylenephosphonic acid (DOTMP).

Embodiment 12c is the method of Embodiment 12b, wherein the chelant comprises 1,4,7,10-tetraazacyclododecane-N,N',N",N'''-tetraacetic acid (DOTA).

Embodiment 12d is the method of Embodiment 12b, wherein the chelant comprises deferoxamine (DFO).

Embodiment 13 is a method of labeling a polypeptide, preferably an antibody or an antigen binding fragment thereof, with a radiometal ion, preferably $^{225}$Ac, $^{111}$In or $^{89}$Zr, the method comprising:

a. providing a modified polypeptide, preferably a modified antibody or antigen binding fragment thereof comprising the polypeptide or antibody or antigen binding fragment thereof covalently linked to an azide, tetrazine or tetrazole group;

b. providing a radiocomplex comprising the radiometal ion, preferably $^{225}$Ac, $^{111}$In or $^{89}$Zr, associated with a chelating moiety, wherein the chelating moiety comprises a chelant covalently linked to an alkyne or an alkene group; and c. contacting the modified polypeptide or antibody or antigen binding fragment thereof with the radiocomplex under a condition to allow the azide, tetrazine or tetrazole group to react with the alkyne or the alkene group to thereby label the polypeptide or antibody or antigen binding fragment thereof with the radiometal ion, preferably $^{225}$Ac, $^{111}$In or $^{89}$Zr, wherein the chelant comprises a structure of formula (I):

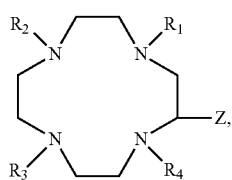

formula (I)

wherein each of $R_1$, $R_2$, $R_3$ and $R_4$ is independently $CHQCO_2X$, wherein
Q is independently hydrogen, $C_1$-$C_4$ alkyl or ($C_1$-$C_2$ alkyl) phenyl, and
X is independently hydrogen, benzyl, $C_1$-$C_4$ alkyl; and
Z is $(CH_2)_nY$, wherein
n is 1-10, and
Y is an electrophilic or nucleophilic moiety covalently linked to the alkyne group; alternatively, Z is hydrogen; and
each of $R_1$, $R_2$, $R_3$ and $R_4$ is independently $CHQCO_2X$, wherein
Q is independently hydrogen, $C_1$-$C_4$ alkyl or ($C_1$-$C_2$ alkyl) phenyl, and
X is independently hydrogen, benzyl, $C_1$-$C_4$ alkyl, or an electrophilic or nucleophilic moiety covalently linked to the alkyne group.

Embodiment 13a is the method of Embodiment 13, wherein the chelant comprises 1,4,7,10-tetraazacyclododecane-N,N',N'',N'''-tetraacetic acid (DOTA).

Embodiment 13b is the method of Embodiment 13, wherein the chelating moiety comprises the structure of formula (II):

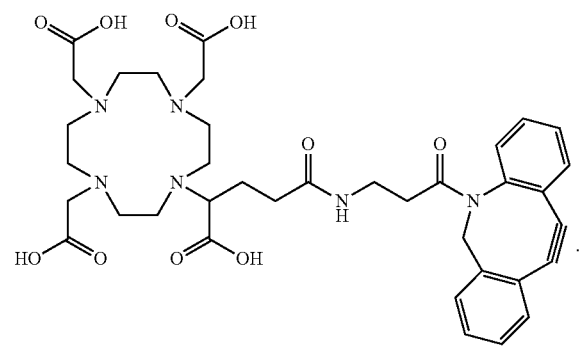

formula (II)

Embodiment 13d is a method of labeling a polypeptide, preferably an antibody or an antigen binding fragment thereof, with a radiometal ion, preferably $^{225}$Ac, $^{111}$In or $^{89}$Zr, the method comprising:

a. providing a modified polypeptide, preferably a modified antibody or antigen binding fragment thereof comprising the polypeptide or antibody or antigen binding fragment thereof covalently linked to an azide, tetrazine or tetrazole group;

b. providing a radiocomplex comprising the radiometal ion, preferably $^{225}$Ac, $^{111}$In or $^{89}$Zr, associated with a chelating moiety, wherein the chelating moiety comprises a chelant covalently linked to an alkyne or an alkene group; and c. contacting the modified polypeptide or antibody or antigen binding fragment thereof with the radiocomplex under a condition to allow the azide, tetrazine or tetrazole group to react with the alkyne or the alkene group to thereby label the polypeptide or antibody or antigen binding fragment thereof with the radiometal ion, preferably $^{225}$Ac, $^{111}$In or $^{89}$Zr, wherein the chelant comprises an open chain ligand, preferably deferoxamine (DFO).

Embodiment 14 is the method of any one of Embodiments 13 to 13c, wherein the chelant is covalently linked to the alkyne or an alkene group via a linker.

Embodiment 15 is the method of any one of Embodiments 13 to 14, further comprising reacting an electrophile on a side chain, preferably the amino side chain of a lysine on or introduced to the polypeptide, preferably the antibody or antigen binding fragment thereof, with a sulfhydryl group covalently linked to the azide, preferably NHS-azide, to obtain the modified polypeptide or antibody or antigen binding fragment thereof.

Embodiment 16 is the method of any one of Embodiments 13 to 15, wherein the polypeptide, preferably antibody or antigen binding fragment thereof, is covalently linked to the azide via a linker.

Embodiment 17 is the method of Embodiment 13, wherein the polypeptide is an antibody or antigen binding fragment thereof, the radiometal ion is $^{225}$Ac, $^{111}$In or $^{89}$Zr, and the chelating moiety comprises the structure of formula (II):

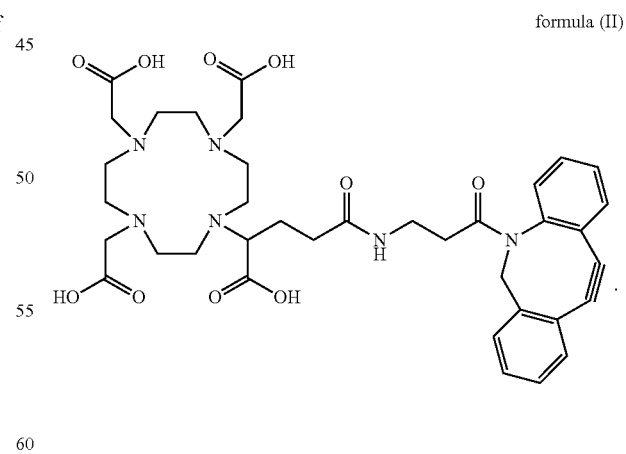

formula (II)

Embodiment 17a is the method of Embodiment 13c, wherein the polypeptide is an antibody or antigen binding fragment thereof, the radiometal ion is $^{225}$Ac, $^{111}$In or $^{89}$Zr, and the chelating moiety comprises the structure of formula (III):

formula (III)

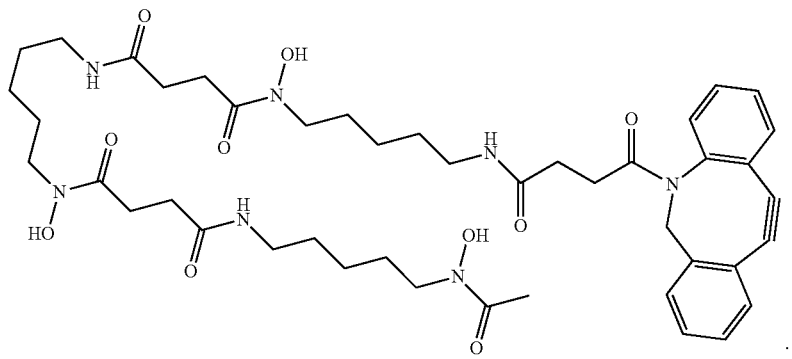

Embodiment 17 is the method of any one of Embodiments 13 to 17a, wherein the polypeptide is an antibody that binds to human prostate-specific membrane antigen (PSMA) or an antigen binding fragment thereof, preferably the antibody comprises a HC CDR1 sequence of SEQ ID NO: 3, a HC CDR2 sequence of SEQ ID NO: 4, a HC CDR3 sequence of SEQ ID NO: 5, a light chain (LC) CDR1 sequence of SEQ ID NO: 6, a LC CDR2 sequence of SEQ ID NO: 7, and a LC CDR3 sequence of SEQ ID NO: 8.

Embodiment 17c is the method of Embodiment 17b, wherein the antibody comprises a HC sequence of SEQ ID NO: 9 and a LC sequence of SEQ ID NO: 10.

Embodiment 18 is a method of dually labeling a polypeptide with two radiometal ions, the method comprising:
a. providing a modified polypeptide comprising the polypeptide covalently linked to a first click reaction partner and a second click reaction partner;
b. providing a first radiocomplex comprising the first radiometal ion associated with a chelating moiety, wherein the chelating moiety comprises a chelant covalently linked to a third click reaction partner; and
c. providing a second radiocomplex comprising the second radiometal ion associated with a chelating moiety, wherein the chelating moiety comprises a chelant covalently linked to a fourth click reaction partner; and
d. contacting the modified polypeptide with the first and second radiocomplexes under a condition to allow the first click reaction partner to react with the third click reaction partner, and the second click reaction partner to react with the fourth click reaction partner, to thereby label the polypeptide with the first and second radiometal ions.

Embodiment 19 is the method of Embodiment 18, wherein one of the first and second click reaction partners comprises an alkyne group, and the other of the first and second click reaction partner comprises an azide, and wherein one of the third and fourth click reaction partners comprises an alkene group, and the other of the third and fourth click reaction partner comprises a diene.

Embodiment 20 is the method of Embodiment 18 or 19, wherein the first or second radiometal ion is a diagnostic emitter, and the other is a therapeutic emitter.

Embodiment 21 is the method of Embodiment 18 or 19, wherein both the first and second radiometal ions are therapeutic emitters.

Embodiment 21a is the method of Embodiment 20 or 21, wherein the diagnostic emitter is $^{62}$Cu, $^{64}$Cu, $^{67}$Ga, $^{68}$Ga, $^{86}$Y, $^{89}$Zr, or $^{111}$In.

Embodiment 21b is the method of any one of Embodiments 20 to 21a, wherein the therapeutic emitter is $^{32}$P, $^{47}$Sc, $^{67}$Cu, $^{77}$As, $^{89}$Sr, $^{90}$Y, $^{99}$Tc, $^{105}$Rh, $^{109}$Pd, $^{111}$Ag, $^{131}$I, $^{153}$Sm, $^{159}$Gd, $^{165}$Dy, $^{166}$Ho, $^{169}$Er, $^{177}$Lu, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{225}$Ac, $^{255}$Fm or $^{227}$Th.

Embodiment 22 is a pharmaceutical composition comprising a radiolabeled polypeptide prepared by a method of any one of Embodiments 1 to 21b and a pharmaceutically acceptable carrier.

Embodiment 23 is a method of treating or diagnosing a disease or disorder, particularly a neoplastic disease or disorder, in a subject in need thereof, comprising administering to the subject the pharmaceutical composition of Embodiment 22.

Embodiment 24 is the method of Embodiment 23, wherein the pharmaceutical composition comprises two compositions to be administered sequentially, the first comprising the modified polypeptide, and the second comprising the radiocomplex or radiocomplexes.

Embodiment 25 is a theranostic agent comprising a radiolabeled antibody prepared by a method of any one of Embodiments 1 to 21b and a pharmaceutically acceptable carrier, wherein the immunological properties of the radiolabeled antibody are preserved.

Embodiment 26 is the theranostic agent of Embodiment 25, wherein the radiometal ion is a diagnostic emitter, preferably $^{89}$Zr.

Embodiment 27 is the theranostic agent of Embodiment 25, wherein the radiometal ion is a therapeutic emitter, preferably $^{225}$Ac.

Embodiment 27a is the theranostic agent of Embodiment 25, wherein the radiometal ion is $^{111}$In.

Embodiment 27b is the theranostic agent of any one of Embodiments 25 to 27a, wherein the polypeptide is antibody that binds to human prostate-specific membrane antigen (PSMA) or an antigen binding fragment thereof, preferably the antibody comprises a HC CDR1 sequence of SEQ ID NO: 3, a HC CDR2 sequence of SEQ ID NO: 4, a HC CDR3 sequence of SEQ ID NO: 5, a light chain (LC) CDR1 sequence of SEQ ID NO: 6, a LC CDR2 sequence of SEQ ID NO: 7, and a LC CDR3 sequence of SEQ ID NO: 8.

Embodiment 27c is the theranostic agent of Embodiment 27b, wherein the antibody comprises a HC sequence of SEQ ID NO: 9 and a LC sequence of SEQ ID NO: 10.

Embodiment 27d is the theranostic agent of any one of Embodiments 25 to 27c, wherein the radiolabeled antibody has the formula of formula (IV):

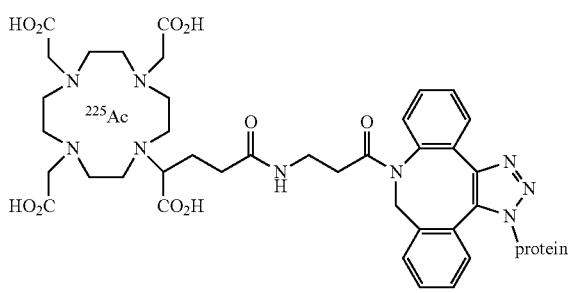

formula (IV) (DOTA-Ac-DBCO-protein), alternatively, the $^{225}$Ac is substituted with another radiometal ion, such as $^{32}$P, $^{47}$Sc, $^{67}$Cu, $^{77}$As, $^{89}$Sr, $^{90}$Y, $^{99}$Tc, $^{105}$Rh, $^{109}$Pd, $^{111}$Ag, $^{131}$I, $^{153}$Sm, $^{159}$Gd, $^{165}$Dy, $^{166}$Ho, $^{169}$Er, $^{177}$Lu, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{255}$Fm, $^{227}$Th, $^{62}$Cu, $^{64}$Cu, $^{67}$Ga, $^{68}$Ga, $^{86}$Y, $^{89}$Zr, or $^{111}$In.

Embodiment 27e is the theranostic agent of any one of Embodiments 25 to 27c, wherein the radiolabeled antibody has the formula of formula (V):

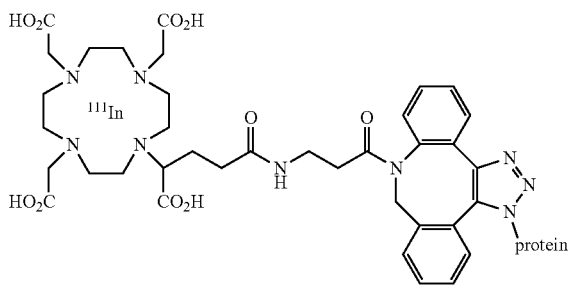

formula (V) (DOTA-In-DBCO-protein).

Embodiment 27f is the theranostic agent of any one of Embodiments 25 to 27c, wherein the radiolabeled antibody has the formula of formula (VI):

$^{111}$Ag, $^{131}$I, $^{153}$Sm, $^{159}$Gd, $^{165}$Dy, $^{166}$Ho, $^{169}$Er, $^{177}$Lu, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{225}$Ac, $^{255}$Fm, $^{227}$Th, $^{62}$Cu, $^{64}$Cu, $^{67}$Ga, $^{68}$Ga, $^{86}$Y, or $^{111}$In.

Embodiment 27g is the theranostic agent of any one of Embodiments 25 to 27c, wherein the radiolabeled antibody has the formula of formula (VII):

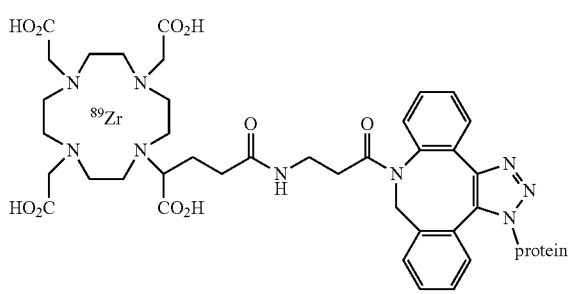

formula (VII) (DOTA-Zr-DBCO-protein).

Embodiment 27h is the theranostic agent of any one of Embodiments 25 to 27g, wherein the radiolabeled antibody has a chelator:antibody ratio (CAR) of less than 3.

Embodiment 27i is the theranostic agent of any one of Embodiments 25 to 27h, wherein the radiolabeled antibody has a chelator:antibody ratio (CAR) of 2.

Embodiment 28 is a combination, preferably a kit, comprising:
a. a modified polypeptide comprising a polypeptide covalently linked to a first click reaction partner; and
b. a radiocomplex comprising a radiometal ion associated with a chelating moiety, wherein the chelating moiety comprises a chelant covalently linked to a second click reaction partner;
wherein the combination is to be used for labeling the polypeptide with the radiometal ion.

Embodiment 28a is the combination or kit of Embodiment 28, wherein the chelant comprises a macrocycle.

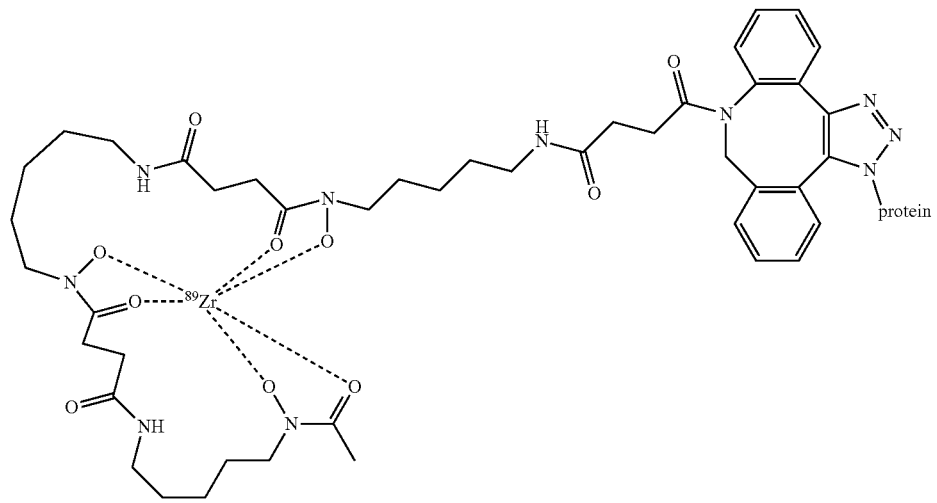

formula (VI) (DFO-Zr-DBCO-protein), alternatively, the $^{89}$Zr is substituted with another radiometal ion, such as $^{32}$P, $^{47}$Sc, $^{67}$Cu, $^{77}$As, $^{89}$Sr, $^{90}$Y, $^{99}$Tc, $^{105}$Rh, $^{109}$Pd, Embodiment 28b is the combination or kit of Embodiment 28, wherein the chelant comprises an open chain ligand.

Embodiment 29 is the combination or kit of Embodiment 28, which is to be used for labeling the polypeptide with the radiometal ion via a reaction between the first and second click reaction partners in vitro.

Embodiment 30 is the combination or kit of Embodiment 28, which is to be used for labeling the polypeptide with the radiometal ion via a reaction between the first and second click reaction partners in vivo.

Embodiment 31 is a composition comprising a modified polypeptide comprising a polypeptide covalently linked to a first click reaction partner.

Embodiment 32 is a composition comprising a radiocomplex comprising a radiometal ion associated with a chelating moiety, wherein the chelating moiety comprises a chelant covalently linked to a second click reaction partner.

Embodiment 32a is the composition of Embodiment 32, wherein the chelant comprises a macrocycle.

Embodiment 32b is the composition of Embodiment 32, wherein the chelant comprises an open chain ligand.

Embodiment 33 is the combination or kit of any one of Embodiments 28 to 30 or the composition of Embodiment 31 or 32, wherein the polypeptide is an antibody or an antigen binding fragment thereof.

Embodiment 33a is the combination or kit or the composition of Embodiment 33, wherein the antibody is capable of binding to human prostate-specific membrane antigen (PSMA) or an antigen binding fragment thereof, preferably the antibody comprises a HC CDR1 sequence of SEQ ID NO: 3, a HC CDR2 sequence of SEQ ID NO: 4, a HC CDR3 sequence of SEQ ID NO: 5, a light chain (LC) CDR1 sequence of SEQ ID NO: 6, a LC CDR2 sequence of SEQ ID NO: 7, and a LC CDR3 sequence of SEQ ID NO: 8.

Embodiment 33b is the combination or kit or the composition of Embodiment 33a, wherein the antibody comprises a HC sequence of SEQ ID NO: 9 and a LC sequence of SEQ ID NO: 10.

Embodiment 33c is the combination or kit or the composition of Embodiment 33a or 33b, wherein the antibody or antigen binding fragment thereof is covalently linked to an azide group.

Embodiment 33d is the combination or kit or the composition of Embodiment 33c, wherein the antibody or antigen binding fragment thereof is covalently linked to the azide group randomly.

Embodiment 33e is the combination or kit or the composition of Embodiment 33c, wherein the antibody or antigen binding fragment thereof is covalently linked to the azide group site specifically.

Embodiment 33f is the combination or kit or the composition of Embodiment 33e, wherein the antibody or antigen binding fragment thereof is covalently linked to the azide group via a method comprising: trimming the antibody or antigen binding fragment thereof with a bacterial endoglycosidase specific for the β-1,4 linkage between the core GlcNac residue(s) in the Fc-glycosylation site(s) of the antibody to obtain a trimmed antibody or antigen binding fragment thereof, and reacting the trimmed antibody or antigen binding fragment thereof with an azide sugar, preferably UDP-GalNaz azido sugar substrate, in the presence of a sugar transferase, preferably GalT galactosyltransferase.

Embodiment 33g is the combination or kit or the composition of Embodiment 33e, wherein the modified antibody or antigen binding fragment thereof is obtained by a method comprising deglycosylating the antibody or antigen binding fragment thereof with an amidase to obtain a deglycosylated antibody or antigen binding fragment thereof, and reacting the deglycosylated antibody or antigen binding fragment thereof with an azido amine, preferably 3-azido propylamine, in the presence of a microbial transglutaminase.

Embodiment 34 is the combination, kit or composition of any one of Embodiments 33 to 33g, wherein the radiometal ion comprises $^{225}$Ac, $^{111}$In or $^{89}$Zr.

Embodiment 35 is the combination, kit or composition of Embodiment 34, wherein the chelant comprises a macrocycle, preferably a structure of formula (I):

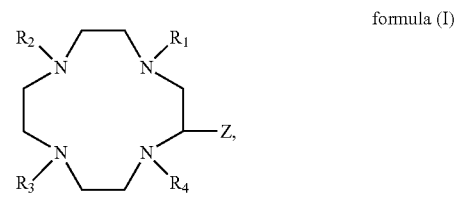

formula (I)

wherein each of $R_1$, $R_2$, $R_3$ and $R_4$ is independently CHQCO$_2$X, wherein Q is independently hydrogen, $C_1$-$C_4$ alkyl or ($C_1$-$C_2$ alkyl) phenyl, and X is independently hydrogen, benzyl, $C_1$-$C_4$ alkyl; and Z is (CH$_2$)$_n$Y, wherein n is 1-10, and Y is an electrophilic or nucleophilic moiety covalently linked to the alkyne group; alternatively, Z is hydrogen; and each of $R_1$, $R_2$, $R_3$ and $R_4$ is independently CHQCO$_2$X, wherein Q is independently hydrogen, $C_1$-$C_4$ alkyl or ($C_1$-$C_2$ alkyl) phenyl, and X is independently hydrogen, benzyl, $C_1$-$C_4$ alkyl, or an electrophilic or nucleophilic moiety covalently linked to the alkyne group.

Embodiment 36 is the combination, kit or composition of Embodiment 35, wherein the electrophilic or nucleophilic moiety is covalently linked to the alkyne group via a linker.

Embodiment 37 is the combination, kit or composition of Embodiment 35 or 36, wherein the chelating moiety comprises a structure of formula (II):

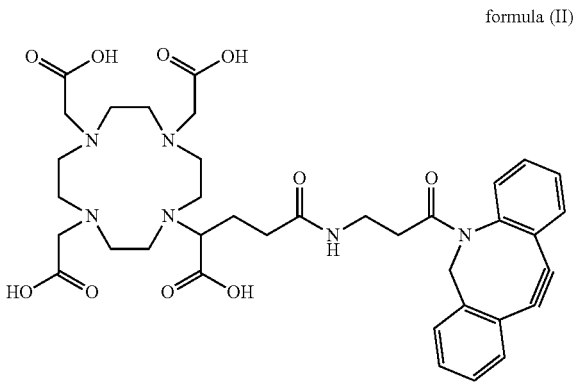 [SMILES: O=C(O)CN1CCN(CC(=O)O)CCN(C(CCC(=O)NCCC(=O)N2Cc3ccccc3C#Cc3ccccc32)C(=O)O)CCN(CC(=O)O)CC1]

formula (II)

Embodiment 37a is the combination, kit or composition of Embodiment 34, wherein the chelating moiety comprises a chelant having an open chain ligand, preferably the chelating moiety comprises a structure of formula (III):

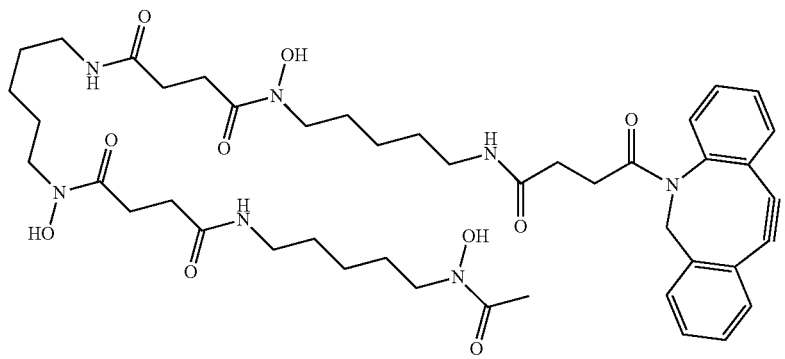

formula (III)

Embodiment 38 is the combination, kit or composition of any one of Embodiments 34 to 37, wherein the polypeptide is covalently linked to the azide via a linker.

Embodiment 39 is a method of treating or diagnosing a disease or disorder, particularly a neoplastic disease or disorder, in a subject in need thereof, comprising administering to the subject the theranostic agent of any one of Embodiments 25-27d, or the combination of anyone of Embodiments 28 and 33 to 38.

Embodiment 40 is a method of treating or diagnosing a disease or disorder, particularly a neoplastic disease or disorder, in a subject in need thereof, comprising administering to the subject the composition of Embodiment 31 and the composition of Embodiment 32, preferably the polypeptide is an antibody.

EXAMPLES

The following examples of the invention are to further illustrate the nature of the invention. It should be understood that the following examples do not limit the invention and that the scope of the invention is to be determined by the appended claims.

Example 1: Random Conjugation of Azide/Handle to an Antibody

Monoclonal Antibodies (mAbs):

A human IgG4 antibody that binds to human prostate-specific membrane antigen (PSMA), referred to herein as "anti-PSMA mAb" with designation "PSMB127", has a heavy chain (HC) CDR1 sequence of SEQ ID NO: 3, a HC CDR2 sequence of SEQ ID NO: 4, a HC CDR3 sequence of SEQ ID NO: 5, a light chain (LC) CDR1 sequence of SEQ ID NO: 6, a LC CDR2 sequence of SEQ ID NO: 7, and a LC CDR3 sequence of SEQ ID NO: 8, and has a HC sequence of SEQ ID NO: 9 and a LC sequence of SEQ ID NO: 10. Anti-PSMA mAb was expressed and purified using standard chromatography methods.

A human IgG4 S228P/F234A/L235A (IgG4-PAA) antibody isotype control for the anti-PMSA mAb, referred to herein as "control mAb", has a HC sequence of SEQ ID NO: 1 and a LC sequence of SEQ ID NO: 2. The commercial antibodies trastuzumab (Herceptin®), cetuximab (Erbitux®), pertuzumab (Perjeta®), and panitumumab (Vectibix®) were purchased from Roche, Lilly, Roche, and Amgen respectively. Mouse anti-human Her2 mAb was obtained from BioXCell (catalog #BE0277). Trastuzumab, pertuzumab, and anti-human Her2 mAb bind to human Her2. Cetuximab and panitumumab bind to human EGFR.

Conjugation:

A stock solution of the antibody (1-10 mg/mL) in 10 mM sodium acetate pH 5.2, phosphate-buffered saline pH 7, or other compatible buffer was mixed with 20% (v/v) of 1 M sodium carbonate buffer pH 9 to a final pH of ~9. NHS-PEG4-azide (Thermo catalog #26130) was dissolved in DMSO to a final concentration of 100 mM, and 0.2% (v/v) of the stock was added to produce a molar excess of ~3-10 relative to the mAb. The reaction was incubated at 22° C. for 10 minutes followed by quenching with the addition of 1 M Tris pH 7.5 to a final concentration of 50 mM Tris.

Purification:

The azide-mAb conjugate was purified and exchanged into a compatible buffer (PBS; 20 mM HEPES 150 mM, NaCl pH 7.5; or 10 mM sodium acetate pH 5.2) using a method such as Zeba® desalting columns with 7K MW cutoff (Thermo), dialysis; standard protein A affinity chromatography; or another compatible method. After purification, the conjugate was concentrated to 10-20 mg/mL using Amicon concentrators with 50K MW cutoff (Millipore®).

Lc/Ms Analysis:

The chelator:antibody ratio (CAR) was determined by LC/MS analysis with an Agilent® G6224 MS-TOF instrument equipped with an Agilent® PLRP-S column (300-Angstrom, 2.1×150 mm; catalog #PL1912-3301) (Table 1). The mass spectrum was deconvoluted using the maximum entropy algorithm over the m/z range 2000-3200 for the masses 140-170 kDa.

Analytical Size-Exclusion Chromatography (SEC):

Analytical SEC was performed to determine the oligomeric state of the antibodies and antibody conjugates and ensure that the conjugation process had not led to aggregation. An Agilent® 1200 series HPLC equipped with a Tosoh® TSKgel G3000SWxl (Tosoh Bioscience® #08541) 7.8 mm×30 cm column was used; mobile phase 1×PBS; flow rate 0.8 ml/ml; injection volume 15 µL; protein concentration 0.1-2 mg/mL.

TABLE 1

| Conjugation efficiency | | |
|---|---|---|
| Antibody | Isotype | CAR |
| anti-PSMA mAb | Human IgG4 | 2.4 |
| control mAb | Human IgG4 | 2.0 |
| Trastuzumab | Humanized IgG1 | 2.5 |

TABLE 1-continued

Conjugation efficiency

| Antibody | Isotype | CAR |
|---|---|---|
| Cetuximab | Chimeric human/mouse IgG1 | 3.6 |
| Pertuzumab | Humanized IgG1 | 2.3 |
| Panitumumab | Human IgG2 | 3.0 |
| Anti-human Her2 | Mouse IgG2a | 3.1 |

Example 2: Random Conjugation of Azide/Handle to Non-Antibody Polypeptides

Non-Antibody Polypeptides:

Transferrin, human holo-Transferrin was purchased from R&D Systems® (catalog #2914-HT) and dissolved in water to 10 mg/mL. EGF, human epidermal growth factor (EGF) was purchased from Sino Biological® (catalog #10605-HNAE).

Conjugation:

A stock solution of the polypeptides (1-10 mg/mL) in 10 mM sodium acetate pH 5.2, phosphate-buffered saline pH 7, or other compatible buffer, was mixed with 20% (v/v) of 1 M sodium carbonate buffer pH 9 to a final pH of ~9. NHS-PEG4-azide (Thermo catalog #26130) was dissolved in DMSO to a final concentration of 100 mM, and 0.2% (v/v) of the stock was added to produce a molar excess of ~3-10 relative to the protein. The reaction was incubated at 22° C. for 10 minutes followed by quenching with 1 M Tris pH 7.5 to a final concentration of 50 mM. The conjugation efficiency is shown in Table 2.

TABLE 2

Conjugation Efficiency

| Protein | Chelator:protein ratio |
|---|---|
| Transferrin | 3.6 |
| EGF | 1.1 |

Example 3: Site-Specific Incorporation of Azido Sugars into Antibody Glycans

Antibody glycans were trimmed with GlycINATOR® (Genovis), a bacterial endoglycosidase specific for the β-1,4 linkage between the core GlcNac residues in the Fc-glycosylation site(s) leaving the inner most GlcNAc intact on the Fc, which can then be used for site-specific incorporation of azido sugars. More specifically, immobilized GlycINATOR® on agarose beads packed into a column (Genovis) was equilibrated in Tris-buffered saline pH 7.4 (TBS). 1 mL of mAb at 5-10 mg/mL was added to the resin and incubated on a rocker for 1 hour at RT. mAb was eluted by spinning at 100×g for 1 minute. The column was eluted 3 more times with 0.5 mL TBS. The elutions containing trimmed mAb were pooled, and the supplied buffer additive (Genovis) was added along with UDP-GalNaz azido sugar substrate and GalT galactosyltransferase enzyme. The reaction was incubated overnight at 30° C. The final azido mAb was purified using a mAb Select column (GE) on an AKTA Avant instrument. Azide modification was confirmed by LC-MS with the CAR determined to be exactly 2.

Example 4: Site-Specific Incorporation of 3-Azido Propylamine with Microbial Transglutaminase (MTG)

Azido groups were installed site-specifically on the antibody at positions Gln295 essentially as described (Dennler et al. Transglutaminase-based chemo-enzymatic conjugation approach yields homogeneous antibody-drug conjugates. Bioconj Chem 2014 Mar. 19; 25(3): p. 569-78). Anti-PSMA mAb was deglycosylated with Rapid PNGase F (New England Biolabs®), an amidase which cleaves between the innermost GlcNAc and asparagine residues of high mannose, hybrid, and complex oligosaccharides and allows for complete deglycosylation and release of all N-glycans, including N-glycans from both conserved (e.g., Fc Asn297) and non-conserved (e.g., Fab N-glycans) glycosylation sites. 10 mL of antibody at 1 mg/mL in sodium acetate buffer pH 5.2 was incubated with 5 µL of PNGase F overnight at 37° C., and deglycosylation was confirmed by LC-MS. PNGase F was removed by 4 cycles of concentration and dilution with an Amicon device (50 kDa cutoff). For conjugation of 3-azido propylamine (3-APA; Click Chemistry Tools®), the deglycosylated mAb (0.5-1 mg/mL) was brought to pH 7-7.5 by addition of 2% (v/v) of 0.5 M HEPES pH 7.5. 100 equivalents of 3-APA were added along with 5-10% w/v of Activa TI transglutaminase (Ajinomoto®), an MTG. The reaction was incubated at 37° C. for 1-4 hours followed by purification of the azide-modified mAb on a mAbSelect Sure column using standard chromatographic methods. The conjugate was characterized by LC-MS and the CAR was determined to be 2.

Example 5: Chelation of Radiometal to Bifunctional Chelator (BFC)

Synthesis of $^{225}$Ac-DOTA-GA-DBCO:

$^{225}$Ac(NO$_3$)$_3$ was purchased from Oak Ridge National Laboratory®. 1,4,7,10-tetraazacyclododececane, 1-(glutaric acid)-4,7,10-triacetic acid-(3-amino-propanoic acid)dibenzocyclo-octyne (DOTA-GA-DBCO) was custom synthesized. The synthesis was based on Bernhard et al. Chem. Eur. J. 2012, 18, 7834-7841. DBCO-amine (3-Amino-1-[(5-aza-3,4,7,8-dibenzocyclooct-1-yne)-5-yl]-1-propanone, Sigma) was reacted with the DOTA-GA anhydride and the product was purified by reverse-phase HPCL.

Quantification of Actinium-225 was achieved using a Capintec® CRC-55TW dose calibrator whereby $^{225}$Ac (NO$_3$)$_3$ dissolved in 0.1 N HCl to make a 10 mCi/mL solution. To a solution of tetramethylammonium acetate (1 M solution, 7.5 µL, 7.5 µmol), DOTA-GA-DBCO (1 mg/mL in water, 2.5 µL, 3.4 nmol) and NaOH (0.1 N, 2.5 µL, 0.25 µmol) in a plastic vial was added to $^{225}$Ac(NO$_3$)$_3$ (10 mCi/mL in 0.1 N HCl, 5 µL, 50 µCi, 0.0038 nmol). The pH of the mixture was observed to be ~6.5 by pH paper. The vial was placed on a shake block at 80° C. and 290 rpm for 30 min., and the vial was allowed to cool to room temperature.

Synthesis of $^{111}$In-DOTA-GA-DBCO:

$^{111}$InCl3 in 0.05 M HCl was purchased from GE Healthcare®. To a solution of tetramethylammonium acetate (1 M solution, 7.5 µL, 7.5 µmol), DOTA-GA-DBCO (1 mg/mL in water, 2.5 µL, 3.4 nmol) and HCl (0.1 N, 5 µL) in a plastic vial was added $^{111}$InCl$_3$ in 0.05 N HCl (5 µL, 104.3 µCi measured in a Capintec® CRC-55TW dose calibrator, 0.0022 nmol). The pH of the mixture was observed to be ~5.5 by pH paper. The vial was placed on a shake block at 60° C. and 290 rpm for 30 min., and the vial was allowed to cool to room temperature.

Synthesis of $^{89}$Zr-DFO-DBCO:

$^{89}$Zr oxalate was purchased from 3D Imaging. DFO-DBCO was purchased from Macrocyclics (Plano, TX catalog #B-773), dissolved in DMSO to 0.5 mg/mL, and diluted in water to 25 µg/mL.

2 mCi of Zr-89 was transferred to a metal-free microcentrifuge tube, and 1 M oxalic acid was added to reach a total volume of 80 µL. 12 µL of 2 M potassium carbonate was added in 2 µL increments, and the mixture stirred with a pipet tip until bubbling stopped. 120 µL of 1 M HEPES was then added followed by 300 µL of water. The pH of the solution was tested, and additional 2 M potassium carbonate was added to raise the pH to 6-6.5 if necessary. 136 µL of the DFO-DBCO stock (3.4 µg) was added, and the reaction was incubated for 1 hour at RT. The chelate was analyzed by spotting 0.5 µL of the reaction on a TLC Green strip (Biodex) and eluting with 20% NaCl. After elution, the strip was scanned with a PerkinElmer® Cyclone Plus phosphor imager to ensure that the majority of the Zr-89 remained at the baseline, indicating chelation by DFO-DBCO.

Synthesis of $^{89}$Zr-DOTA-GA-DBCO:

To a Waters Sep-pak® Light QMA strong anion exchange cartridge (acrylic acid/acrylamide copolymer on Diol silica, Surface functionality: C(O)NH(CH$_2$)$_3$N(CH$_3$)$_3$$^+$Cl$^-$, 300 Å pore size, 37-55 µm particle size, 230 µeq/gram ion exchange capacity) MeCN (6 mL) was added followed by 0.9% saline (10 mL) then water (10 mL). A solution of $^{89}$Zr(ox)$_2$ in 1.0 M oxalic acid (2 µL, 290 µCi) was added to the pre-conditioned cartridge. The cartridge was in turn washed with de-ionized water (20 ml) to remove excess oxalic acid followed by elution of $^{89}$ZrCl$_4$ off the column with 1.0 M HCl(aq.) (100 µL each) to afford a total volume of 400 µL with recovery of 248 µCi (86%), the majority of activity being in fraction 3. The combined aliquots were then evaporated to dryness.

10 µL of DOTA-GA-DBCO (1.0 mg/mL in metal free water, 10 µg, 13.6 nmol) was added to the $^{89}$ZrCl$_4$ (268 µCi, 50 µL). The solution of DOTA-GA-DBCO/89Zr was diluted in 150 µL of 1.0 M HEPES. The pH of the mixture was adjusted to pH 7.5 (Pandya et al., Zirconium tetraazamacrocycle complexes display extraordinary stability and provide a new strategy for zirconium-89-based radiopharmaceutical development. *Chem Sci.* 2017 Mar. 1; 8(3): p. 2309-2314). The solution was then incubated at 90° C. for 60 min. The yield of 89Zr-DOTA-GA-DBCO complex was determined to be 98% by SPC25 column (Sigma-Aldrich® part number SPC25120-50G) eluted with 1% NH$_4$OH solution. Un-chelated $^{89}$Zr stays on the column, while $^{89}$Zr-DOTA-GA-DBCO complex is eluted out.

Example 6: Synthesis of Click Labeled Radioconjugates of Anti-PSMA mAb

Figure 2:
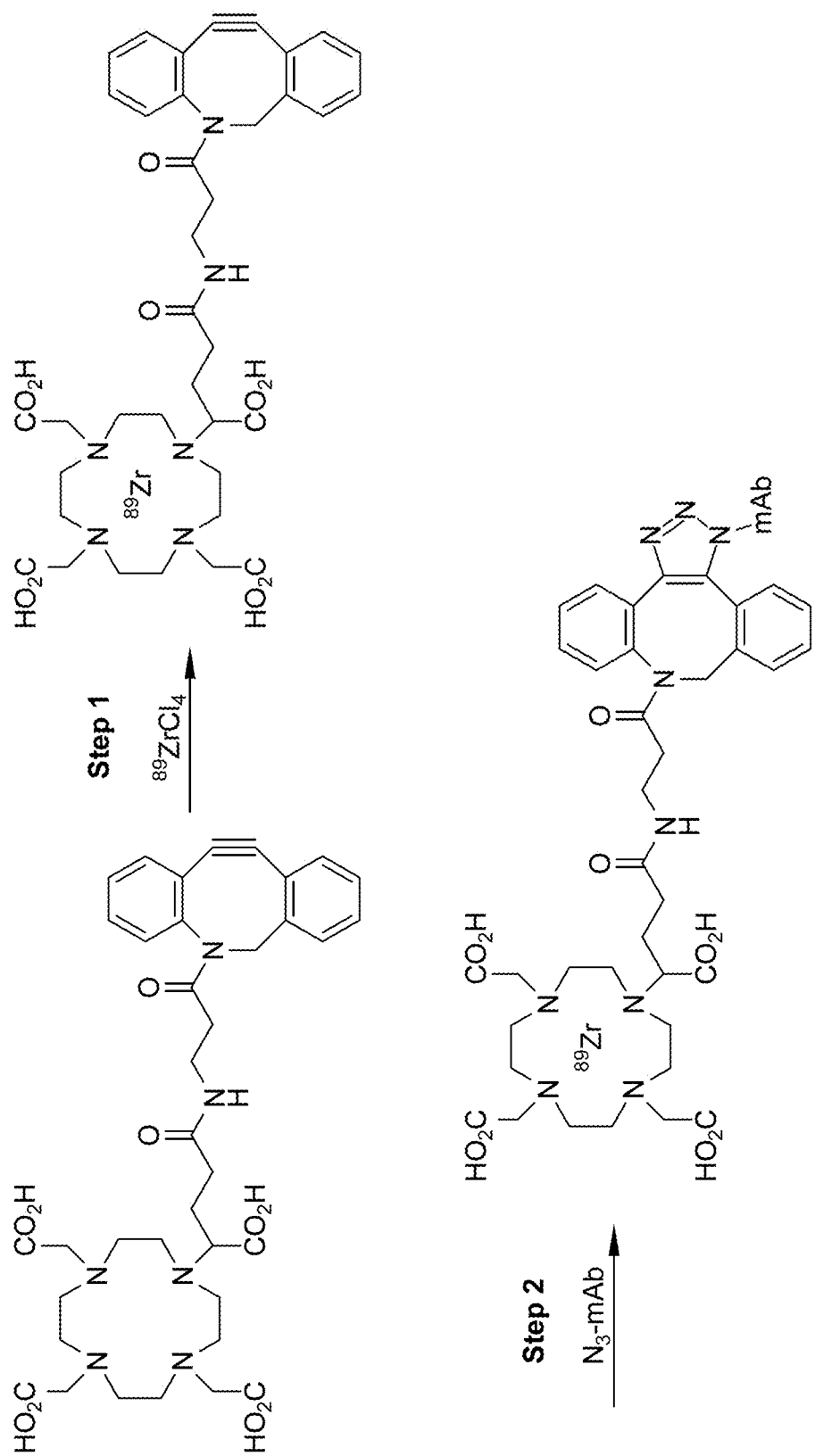
FIG. 2 shows a synthesis scheme of an improved two-step preparation of $^{89}$Zr-DOTA-mAb via click chemistry according to an embodiment of the application.

See FIGS. 1 and 2 for schematics of schematics of radiolabeling antibodies according to methods of the invention.

Synthesis of Anti-PSMA mAb-Dibenzo-[1,2,3]-Triazoloazocine-GA-DOTA-225Ac (Site Specific, CAR=2):

Random or site-specific azide-modified antibody (site-specific, CAR=2 or random, average CAR between 1 and 4) in PBS or other compatible buffer (10-20 mg/mL) was added to the solution of $^{225}$Ac-DOTA-GA-DBCO produced as described. The final pH of the mixture was ~6.5 by pH paper. The reaction solution was gently agitated and allowed to stand still at room temperature for 3 h before purification with a PD-10 column (GE Healthcare®) pre-conditioned with 15 mL of NaOAc buffer, 10 mM, pH 6-6.5 or another compatible buffer. The reaction mixture was pipetted into the reservoir of the pre-conditioned PD-10 column, and the eluate was collected in plastic tubes. The reaction vial was washed with NaOAc buffer (0.2 mL×3), the washings were pipetted into the reservoir of the PD-10 column, and the eluate was collected. NaOAc buffer was continuously applied into the reservoir of the PD-10 column, and the eluate was collected in plastic tubes with each tube collecting ~1 mL of the eluate, until a total of 10 mL of eluate was collected.

The purity of each fraction collected was assessed by iTLC-SG (Agilent®) using citrate-H$_2$O-MeOH solution as the mobile phase. Pure fraction(s) were combined to afford final product in 10 mM NaOAc buffer. The product solution was analyzed by HPLC for chemical and radiochemical purity. The antibody concentration in the product solution was determined by UV absorption using a standard curve. The activity of the product solution was in turn quantified using a Capintec® CRC-55TW dose calibrator.

Quality Control of Ac-225 Chelation:

A chelation challenge was employed using diethylenetriaminepentaacetic acid (DTPA) as a quality control for a purified product. A 10 mM aqueous solution of Na$_5$DTPA was added to a sample solution containing $^{225}$Ac labeled mAb until the [DTPA]/[mAb]=500-1,000. A 50 mM aqueous solution of Na$_5$DTPA was added to an aliquot of the purified product in solution containing $^{225}$Ac labeled mAb until the [DTPA]/[mAb]=50,000-100,000. The two mixtures were placed on a shake block at room temperature and 290 rpm for 30 min. The mixture was spotted on iTLC-SG and developed with citrate-H$_2$O-MeOH solution as the mobile phase. Under these conditions, free $^{225}$Ac migrates to the solvent front and the bound $^{225}$Ac-mAb stays at the baseline.

Synthesis of Anti-PSMA mAb-Dibenzo-[1,2,3]-Triazoloazocine-GA-DOTA-$^{111}$In:

Random or site-specific azide-modified anti-PSMA mAb in 10 mM NaOAc (site-specific, CAR=2 or random, average CAR between 1 and 4) was added to the solution of $^{111}$In-DOTA-GA-DBCO produced as described. The reaction solution was gently agitated and allowed to stand still at room temperature for 2 h before passing through a PD-10 column. The PD-10 column was pre-conditioned by passing 15 mL of NaOAc buffer, 10 mM, pH 6-6.5, through the column, and the washings were discarded. The reaction mixture was then pipetted into the reservoir of the pre-conditioned PD-10 column, and the eluate was collected in plastic tubes. The reaction vial was washed with NaOAc buffer (0.2 mL×3), the washings were pipetted into the reservoir of the PD-10 column, and the eluate was collected. NaOAc buffer was continuously applied into the reservoir of the PD-10 column, and the eluate was collected in plastic tubes with each tube collecting ~1 mL of the eluate, until a total of 10 mL of eluate was collected.

The purity of each fraction collected was assessed by iTLC-SG using 10 mM EDTA aqueous solution (pH=5-6) as the mobile phase. Pure fraction(s) were combined to afford final product in 10 mM NaOAc buffer. The product solution was analyzed by HPLC for chemical and radiochemical purity. The antibody concentration in the product solution was determined by UV absorption using a standard curve. The activity of the product solution was in turn quantified using a Capintec® CRC-55TW dose calibrator.

Quality Control of In-111 Chelation:

A chelation challenge was employed using DTPA as a quality control for a purified product: A 10 mM aqueous solution of Na$_5$DTPA was added to a sample solution containing $^{111}$In labeled mAb until the [DTPA]/[mAb]

=1000-10,000. The mixture was placed on a shake block at room temperature and 290 rpm for 30 min. The mixture was spotted on iTLC-SG and developed with 10 mM EDTA aqueous solution (pH=5-6) as the mobile phase. Free $^{111}$In or loosely bound $^{111}$In migrates to the solvent front and the tightly bound $^{111}$In-mAb stays at the baseline.

Synthesis of Anti-PSMA mAb-Dibenzo-[1,2,3]-Triazoloazocine-DFO-Zr-89

800 μg of random azide-modified anti-PSMA mAb (average CAR between 1 and 4; the same procedure can be carried out with a site-specific azido-mAb) in 10 mM HEPES 50 mM NaCl pH 7.5 or other compatible buffer was added to the solution of $^{89}$Zr-DFO-DBCO produced as described and incubated at 37° C. for 1.5 hrs before passing through a PD-10 column. The PD-10 column was preconditioned by passing 15 mL of isotonic saline through the column, and the washings were discarded. The reaction mixture was then pipetted into the reservoir of the preconditioned PD-10 column, and the eluate was collected in plastic tubes. Saline was continuously applied into the reservoir of the PD-10 column, and the eluate was collected in plastic tubes with each tube collecting 0.5 mL of the eluate, until a total of 10 mL of eluate was collected. Activity of each fraction and of the material remaining on the column was determined with a dose calibrator. The product peak, usually fractions 4-7 was pooled to afford the final product. The product solution was analyzed by HPLC for chemical and radiochemical purity. The antibody concentration in the product solution was determined by UV absorption using a standard curve. The activity of the product solution was quantified using a dose calibrator.

Synthesis of Anti-PMSA mAb-DOTA-$^{89}$Zr

Azide-modified anti-PSMA mAb conjugate (CAR=1-4), modified by random azide conjugation, in 20 mM HEPES 50 mM NaCl pH 7.5 (10.1 mg/mL, 200 μL, ~13.5 nmol) was added to the solution of 89Zr-DOTA-GA-DBCO produced, as described above. The final pH of the mixture was adjusted to 7.0. The reaction solution was incubated at 37° C. for 2 h, followed by purification on a PD-10 column (GE Healthcare®) with either 0.9% saline, a HPES buffer, or PBS to give the product 89Zr-DOTA-mAb in 64%.

Quality Control of Zr-89 Chelation:

For Zr-DFO-mAbs, purified products were analyzed by HPLC only. These conjugates did not retain Zr-89 upon challenge with DTPA or EDTA. Zr-DOTA-mAbs were challenged with the addition of EDTA to 33 mM and incubated overnight at RT. Conjugates were analyzed after challenge by running over a PD-10 column and found to retain 80% of the radioactivity.

Example 7: Analytical Characterization of Click-Labeled Radioconjugates

Determining Radiochemical Conversion

Radiochemical conversion (% RA conversion; see Tables 3-5) was determined by iTLC-SG (Instant Thin Layer Chromatography (iTLC) using a binderless, glass microfiber chromatography paper impregnated with a silica gel (SG)). % RA conversion values are calculated by dividing the integrated value of the product peak's radio signal (of different retention time of radioactive starting material and byproducts) by the value obtained when integrating all radio signal peaks present between the baseline and solvent front. This fraction of product is then expressed as a percentage conversion.

For Ac-225 incorporated products, sample solutions containing ~0.1-1 μCi of $^{22}$Ac were spotted on the baseline of an iTLC-SG strip approximately 2 cm from the bottom edge. The iTLC-SG strip was developed using a citrate-water-methanol mobile phase (20 mL 0.4 M trisodium citrate/3 mL 2 N HCl/2.3 mL MeOH), allowed to dry at room temperature, and stored for a minimum of 6 h before analysis (reaching secular equilibrium of 225Ac and all daughter nuclides). The iTLC-SG was scanned using a Bioscan AR2000 radio-TLC imaging scanner using a 99mTc setting.

For In-111 chelates, sample solutions containing ~0.5-2.5 μCi of $^{111}$In were spotted on the baseline of an iTLC-SG strip, approximately 2 cm from the bottom edge. The iTLC-SG strip was developed using 10 mM sodium EDTA pH 5-6 as the mobile phase and then allowed to dry at room temperature. The dried iTLC-SG was scanned using a Bioscan AR2000 radio-TLC imaging scanner using an In-111 setting.

For Zr-89 chelates the % RA conversion was determined by dividing the activity on the product peak by the total activity including the activity in the PD-10 column, as determined by counting with a dose calibrator.

Determining Radiochemical Purity of Radiolabeled Proteins

Radiochemical purity (% RA purity; see Tables 3-4) of Ac-225 and In-111 chelates was determined by SE-HPLC (size exclusion HPLC). For Ac-225, a Tosoh® TSKgel® column (G3000SW×17.8 mm×30 cm, 5 μm) was used; the column was eluted with DPBS buffer (1×, without calcium and magnesium); flow rate: 0.7 mL/min; 20 min run; room temperature. After HPLC, the eluate was collected in pre-numbered vials with each vial collecting 0.5 min or 1 min of eluate fraction. The eluate-containing vials were left at room temperature for >6 h to allow $^{225}$Ac reach the secular equilibrium with its daughter nuclides. The activity in each vial was then counted in a Capintec® CRC-55TW well counter. The radio-chromatogram was reconstructed based on the activity in the vials.

For In-111, Tosoh® TSKgel® column (G3000SW×17.8 mm×30 cm, 5 μm) was used; the column was eluted with DPBS buffer (1×, without calcium and magnesium); flow rate: 0.7 mL/min; 20 min run; room temperature. Radioactivity detection was accomplished using the above HPLC system and a PerkinElmer® radio flow detector Radiomatic 625TR and equipped with a 0.5 mL flow cell using In-111 setting and Ultima Flo™ M cocktail at a flow rate of 1.4 mL/min.

For Zr-89 (see Table 5), Tosoh® TSKgel® column (G3000SW×17.8 mm×30 cm, 5 um) was used. The column was eluted with citrate-buffered saline; flow rate: 1 mL/min; 20 min run; room temperature. Radioactivity detection was accomplished using the above HPLC system and a Beckman flow through detector coupled to a Bioscan Flow Count instrument.

TABLE 3

Actinium-225 radiolabeling of proteins

| mAb | Step 1* % RA conversion (iTLC) | Step 2** | | | | | |
|---|---|---|---|---|---|---|---|
| | | % RA conversion (iTLC) | % RA purity (HPLC) | Spec. conc. (µCi/mL) | Spec. ac. (µCi/mg) | Total RA (µCi) | CAR |
| anti-PSMA mAb (random azide) | 88% | 73% | 80% | 17.2 | 74.9 | 17.2 | 3-4 |
| anti-PSMA mAb (site specific glycan) | 88% | 77% | 83% | 7.2 | 102.8 | 7.2 | 2 |
| anti-PSMA mAb (site specific MTG) | 93% | 70% | 90% | 31.3 | 74.2 | 31.3 | 2.0 |
| control mAb (random azide) | 92% | 68% | 97% | 28.1 | 56.1 | 28.1 | 2 |
| Panitumumab (random azide) | 87% | 65% | 95% | 24.9 | 66.6 | 24.9 | 3.0 |
| Cetuximab (random azide) | 91% | 67% | 98% | 33.7 | 76.4 | 33.7 | 3.6 |
| hEGF (random azide) | 92% | 48% | 100% | 19.63 | 1091 | 19.63 | 1.1 |
| Transferrin (random azide) | 94% | 57% | 78% | 24.1 | 83.7 | 24.1 | 3.6 |
| Trastuzumab (random azide) | 94% | 60% | 97% | 9.88 | 62.9 | 9.88 | 2.5 |
| Pertuzumab (random azide) | 94% | 63% | 92% | 16.75 | 49.9 | 16.75 | 2.3 |
| Anti-human HER2 (random azide) | 85% | 78% | 94% | 21.5 | 55.0 | 21.5 | 3.1 |

*Step 1 is the chelation of Actinium-225 to DOTA-GA-DBCO
**Step 2 is the click reaction the bifunctional chelate to the protein

TABLE 4

Indium-111 radiolabeling of proteins

| mAb | Step 1* % RA conversion (iTLC) | Step 2** | | | | | |
|---|---|---|---|---|---|---|---|
| | | % RA conversion (iTLC) | % RA purity (HPLC) | Spec. conc. (µCi/mL) | Spec. ac. (µCi/mg) | Total RA (µCi) | CAR |
| anti-PSMA mAb (random azide) | 81% | 79% | 98% | 57.6 | 139.5 | 72 | 2.4 |
| Transferrin (random azide) | 79% | 88% | 90% | 71.4 | 410.3 | 71.4 | 3.6 |
| Panitumumab (random azide) | 46% | 79% | 99% | 82.0 | 279 | 82.0 | 3.0 |
| Cetuximab (random azide) | 74% | 75% | 100% | 51.3 | 290 | 51.3 | 3.6 |

*Step 1 is the chelation of Indium-111 to DOTA-GA-DBCO
**Step 2 is the click reaction the bifunctional chelate to the protein

TABLE 5

Zr-89 radiolabeling of anti-PSMA mAb with DFO-DBCO

| mAb | % RA conversion | % RA purity (HPLC) | Spec. conc. (µCi/mL) | Spec. ac. (µCi/mg) | Total RA (µCi) | CAR |
|---|---|---|---|---|---|---|
| anti-PSMA mAb (random azide) | 47% | 100% | 131 | 1171 | 262 | 2.4 |

Example 8: Click Reaction of Modified mAb with DOTA-GA-DBCO

Random and site-specific azido-mAbs (anti-PSMA mAb, Cetuximab, Panitumumab, Trastuzumab, Pertuzumab) at 1-10 mg/mL were mixed with a 5× to 20× excess of unchelated DOTA-GA-DBCO and incubated at RT or 37° C. for 1-24 hours. mAbs were desalted with Zeba® desalt spin columns (Thermo) and concentrated with an Amicon® centrifuge concentrator (Millipore®), rediluted with buffer and concentrated again to remove any remaining DBCO-DOTA. Complete click reaction of all free azides with DBCO-DOTA was confirmed by LC-MS.

Example 9: Click Reaction of Modified mAb with DFO-DBCO

Random and site-specific anti-PSMA mAb azido-mAbs at 1-10 mg/mL were mixed with a 5× to 20× excess of unchelated DOTA-GA-DFO and incubated at RT or 37° C. for 1-24 hours. mAbs were desalted with Zeba® desalt spin columns (Thermo) and concentrated with an Amicon® centrifuge concentrator (Millipore®), rediluted with buffer and concentrated again to remove any remaining DBCO-DFO. Complete click reaction of all free azides with DBCO-DFO was confirmed by LC-MS.

Example 10: Cell Binding (FACS)

Cell binding of azide-modified antibodies, DOTA-DBCO-azide modified antibodies, and DFO-DBCO-azide modified antibodies was compared to the parental mAbs for the conjugates described in Table 1. Cell lines expressing the mAb target were treated with antibody or conjugate in a range of a concentrations, and binding was measured by flow cytometry. Panitumumab and Cetuximab conjugates were evaluated for binding to EGFR+A431 cells. Herceptin® and Pertuzumab were evaluated for binding to HER2+ SK-BR-3 cells. Anti-PSMA mAb was evaluated for binding to PSMA+C4-2b cells.

Cell Lines:

C4-2B cells, a human prostate carcinoma cell line, were obtained from Janssen® Oncology (Spring House, PA). A431 cells, a human epidermoid carcinoma cell line, and SK-BR-3 cells, a human breast cancer cell line, were obtained from Janssen BioTherapeutics (Spring House, PA) with cells originally from ATCC (Manassas, VA). EGFR Receptor negative MOLM-13 Human Acute Myeloid Leukemia suspension cells were maintained in RPMI1640+25 mM Hepes (Gibco) supplemented with 20% Heat Inactivated Fetal Bovine Serum (Gibco). Cells were grown in RPMI1640+25 mM Hepes (Gibco, Waltham, MA) with 10% FBS (Gibco, Waltham, MA).

Flow Cytometry:

Cells were detached from flask using enzyme free cell dissociation buffer (Gibco, Waltham, MA) and strained through a 40 um filter (Falcon). $5 \times 10^4$ cells were seeded per well in a 96-well u-bottom plate. Cells were incubated with conjugated antibody or parental antibody diluted in BSA stain buffer (BD Bioscience, San Jose, CA) for 1 hr at 4° C. Cells were washed twice with stain buffer. Cells were then incubated in the dark for 30 min at 4° C. with AlexaFluor647 tagged anti-human IgG secondary antibody (Jackson ImmunoResearch Laboratories). Secondary antibodies were diluted 1:200 in stain buffer containing 3% donkey serum (Rockland Immunochemicals). For the last 10 minutes of the incubation SYTOX® Green Nucleic Acid Stain (ThermoFisher) was added to cells at a final concentration of 30 nM. Cells were washed twice with stain buffer then resuspended in a final volume of 25 µL/well in stain buffer and read on the iQue® Screener flow cytometer (Intellicyt®). ForeCyt® software was used to analyze data. Live cells were determined by excluding events with high nucleic acid stain. Mean fluorescence intensity (MFI) was determined on live cells and graphed in GraphPad® Prism 7 (GraphPad® Software) as log of antibody concentration vs. MFI. A non-linear regression curve fit was added to data and $EC_{50}$ values were calculated.

For all mAbs and conjugates tested, the parental mAbs and modified mAbs showed similar cell binding (Table 6).

TABLE 6

EC50s (nM) of mAbs/conjugates binding to target cells

| | mAb | mAb-azide | mAb-DOTA | mAb-DFO |
|---|---|---|---|---|
| Vectibix | 1.3 | 1.3 | 0.9 | |
| Cetuximab | 0.6 | 0.2 | 0.4 | |
| Herceptin | 2.0 | 0.9 | 3.1 | |
| Pertuzumab | 2.5 | 3.3 | 4.4 | |
| anti-PSMA mAb (random azide) | 5.5 | 4.7 | 5.4 | 4.6 |
| anti-PSMA mAb (glycan) | 0.7 | 0.5 | 0.7 | |

MTG samples

| | mAb | Deglycosylated | mAb-azide | mAb-DOTA | mAb-DFO |
|---|---|---|---|---|---|
| anti-PSMA mAb (MTG) | 4.1 | 3.4 | 5.0 | 6.7 | 4.5 |

Example 11: In-111 Cell Binding Assay

Cell binding was measured with a radiometric assay using the In-111 radiolabeled proteins described in Table 4. Anti-PSMA mAb and transferrin were tested on C4-2B cells (PSMA+ and transferrin+). Cetuximab and panitumumab were tested on A431 cells (EGFR+) and MOLM-13 cells (EGFR−).

Adherent cells were detached with Enzyme-Free Cell Dissociation Buffer (Gibco). Detached adherent cells and collected suspension cells were counted and washed with cold Stain Buffer (BD Biosciences). Varying numbers of cells in 200 µL Stain Buffer were added to microcentrifuge tubes and placed on ice. 0.5 µCi of In-111 labeled protein was added to each tube and incubated for 1 hour on ice. Cells were washed with cold PBS (Gibco) to remove unbound antibody and resuspended in 500 µL cold PBS. Samples were transferred to counting vials, and cell-associated radioactivity was determined by gamma counting (Hidex Automatic Gamma Counter).

Counts per minute (CPM) from study samples were converted to µCi of In-111 using CPM value using a linear regression created using known amounts of In-111 labeled protein. µCi Bound Values were converted to Moles Bound using the following calculation: (µCi Bound/Specific Activity)/MW mAb or Protein. Each data point is the mean of duplicate samples.

Click labeled In-111 anti-PSMA mAb and In-111 transferrin bound to C4-2B cells with amounts of cell-associated radioactivity increasing with increasing cell number (FIG.

Figure 3A:
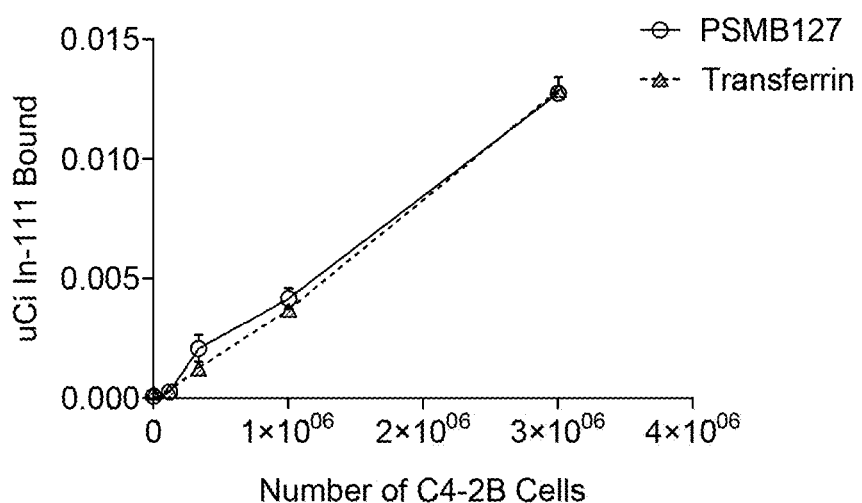
FIG. 3A shows cell binding of In-111 radioimmunoconjugates: bound radioactivity increases with increasing cell number; in particular.
Figure 3B:
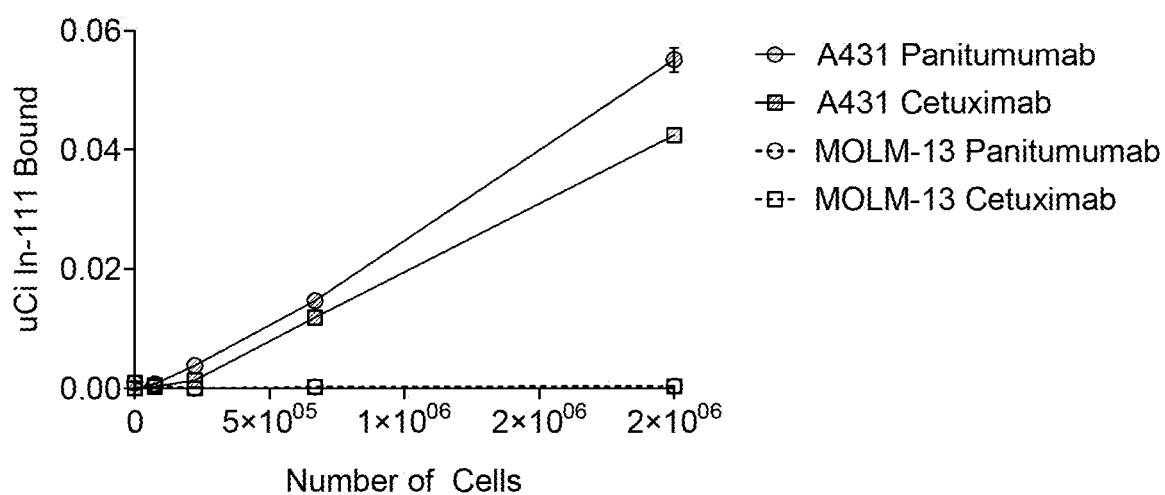
FIG. 3B shows cell binding of In-111 radioimmunoconjugates: bound radioactivity increases with increasing cell number; in particular.

3A). Click labeled In-111 anti-EGFR antibodies Panitumumab and Cetuximab bound to A431 cells with amounts of cell-associated radioactivity increasing with increasing cell number; no specific binding of the click labeled anti-EGFR antibodies was detected with the negative control MOLM-13 cells (FIG. 3B).

Example 12: Indium Cell Uptake Assay

The kinetics of internalization of In-111 click-labeled anti-PSMA mAb in C4-2B cells was determined.

Cells were seeded at $3 \times 10^6$ cells per 60 mm dish (Corning) and placed in 37° C. humidified $CO_2$ incubator overnight. Seeding media was removed and replaced with 2 mL cold Stain Buffer (BD Biosciences). Dishes were then placed on ice. 0.5 µCi In-111 labeled antibody was added to each dish and incubated for 1 hour on ice. Cells were washed with cold PBS (Gibco) to remove unbound antibody from the cell surface. At various timepoints cells were assayed for surface membrane bound radioactivity and intracellular radioactivity as described below.

Surface-bound radioactivity was stripped using an acid wash stripping procedure: 1.5 mL Stripping Buffer (50 mM glycine, 150 mM NaCl pH 2.7 with pepsin (Amresco) added to 25 µg/mL) was added to cells, and dishes were incubated on ice for 15 minutes. Stripping Buffer was transferred to counting vials. Cells were washed with cold PBS, and washes were transferred to counting vials. Radioactivity was assayed by gamma counting (Hidex Automatic Gamma Counter). Surface membrane bound radioactivity was determined as the sum of the Stripping Buffer+PBS Washes.

Intracellular radioactivity was assayed by preparing cell lysates: After surface-bound radioactivity was stripped and cells were washed, 1.5 mL 1 M NaOH (Teknova) was added to cells, and dishes were incubated on ice for 5 minutes. Surface-Stripped Cell Lysates were transferred to counting vials. Dishes were washed with cold PBS, and washes were transferred to counting vials. Radioactivity was assayed by gamma counting (Hidex Automatic Gamma Counter). Intracellular radioactivity was determined as the sum of the Surface-Stripped Cell Lysates+PBS Washes.

For Time=0 samples, cells were assayed for surface membrane bound radioactivity and intracellular radioactivity immediately after initial antibody binding on ice. For 10-minute, 30-minute, 1-hour and 2-hour samples, 3 mL cell culture media was added to each dish after initial antibody binding and dishes were placed in 37° C. humidified $CO_2$ incubator. At each timepoint, dishes were removed from the incubator and placed on ice. Cell culture media was transferred to counting vials, and cells were washed with cold PBS. PBS washes were collected into counting vials. Cells were assayed for surface membrane bound radioactivity and intracellular radioactivity as described. At each timepoint, an Unstripped Sample was generated by incubating cells with PBS instead of Stripping Buffer prior to Cell Lysis. These samples were used to evaluate stripping efficiency and to compare results with Stripped samples.

CPM from study samples were converted to µCi In-111 using CPM value from a linear regression created using known amounts of In-111 labeled mAb. Percent Localization of In-111 mAb on cell surface membrane (stripped samples) and intracellular (lysed samples) was determined using the following formula: % Localized=100*(Sample µCi/Average Total µCi), where Total µCi refers to the addition of all collected samples including incubation media, PBS washes, glycine rinses and lysed cells. Each data point is the mean of duplicate samples.

Figure 4:
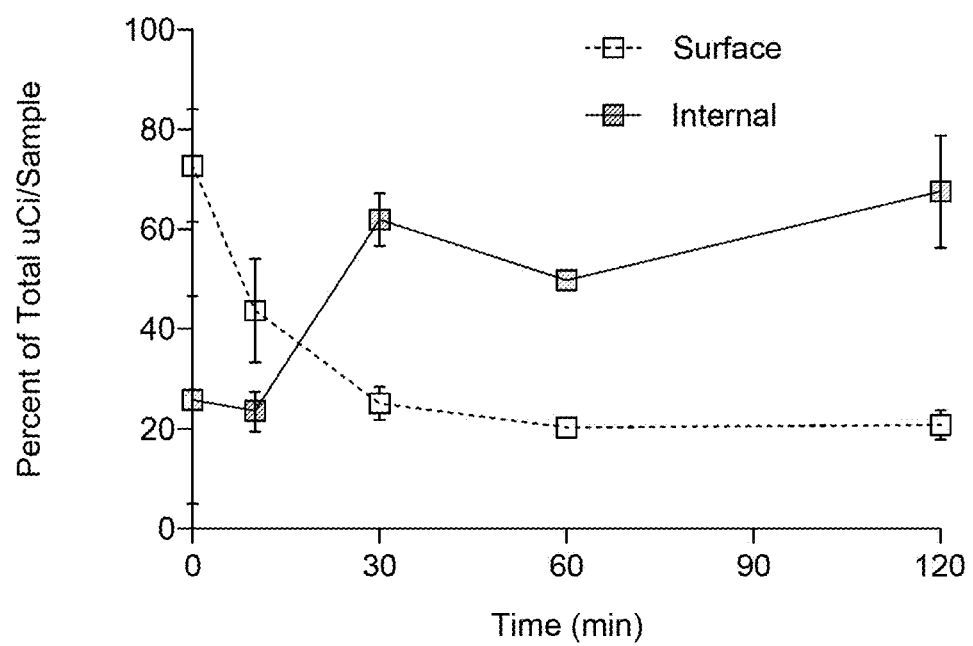
FIG. 4 shows kinetics of cell internalization of In-111 in the human prostate cancer cell line C4-2B treated with a anti-PSMA mAb In-111 radioimmunoconjugate according to an embodiment of the application; surface-bound In-111 rapidly disappeared from the cell surface and was redistributed intracellularly.

Surface bound In-111 rapidly disappeared from the cell surface and was redistributed intracellularly. The stripping technique released 80% of the cell surface associated radioactivity at time 0; by the end of the incubation only 20% was released by stripping and over 60% of the radioactivity was in the cell lysate (FIG. 4).

Example 13: Efficacy in Mouse Tumor Xenograft Model

Dose Ranging Study of Anti-PSMA mAb-DOTA-Ac-225:

Male NSG mice (N=8 per group) were implanted subcutaneously with $10^6$ LNCaP cells, and tumors grew to 100-150 mm$^3$.

Mice were injected intravenously with a single dose of anti-PSMA mAb-azide-DOTA-$^{225}$Ac or isotype control, control mAb-azide-DOTA-$^{225}$Ac at a range of activities (10 nCi, 25 nCi, 70 nCi, 200 nCi). Injected dose per mouse was made up to a total of 10 µg protein with cold antibody. Tumor size and body weight were measured twice-weekly. Animals were euthanized when tumor size exceeded 1,500 mm$^3$, or body weight loss exceeded 20%.

Figure 5A:
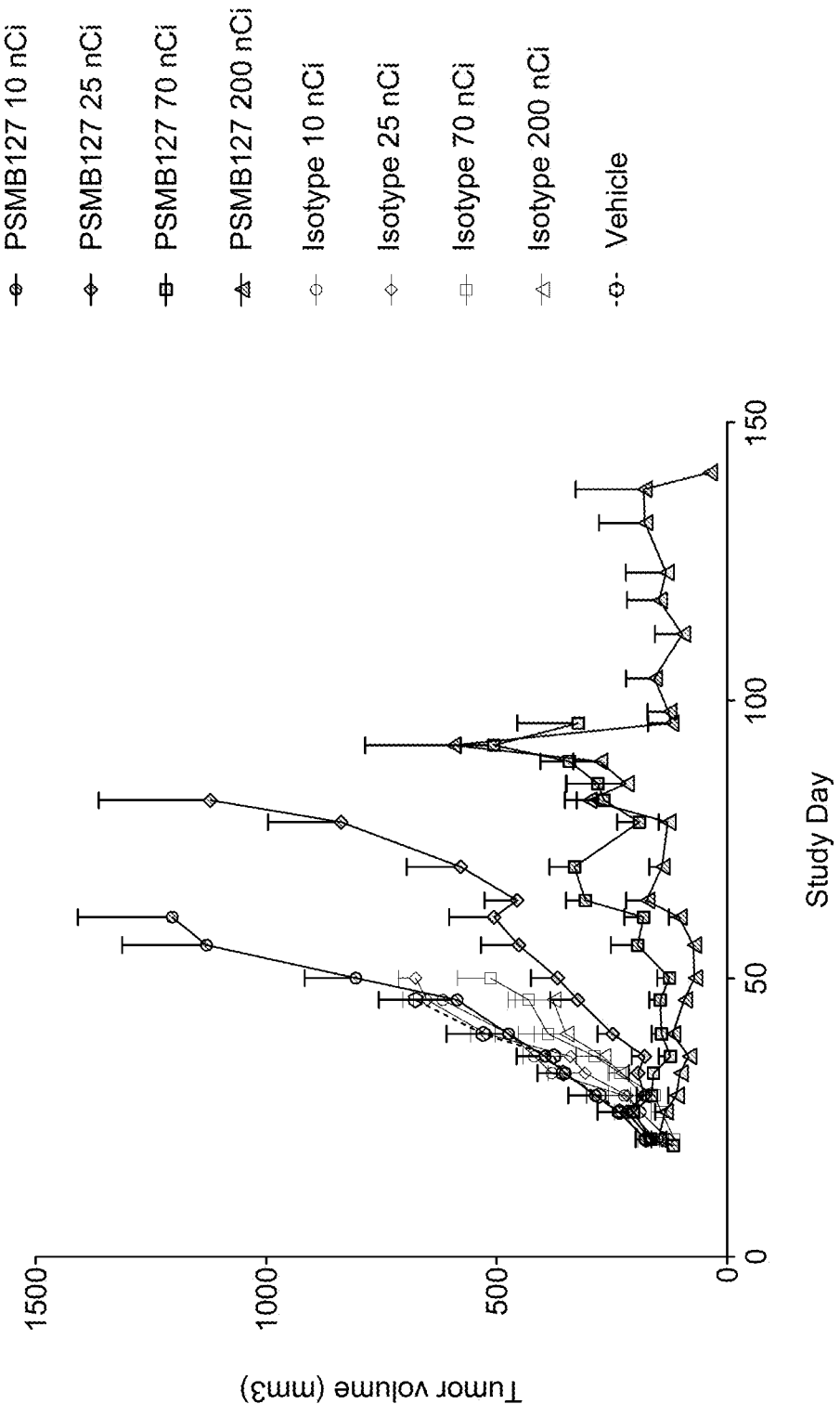
FIG. 5A shows results of a mouse tumor xenograft study; mice were implanted with human prostate cancer LNCaP cells; when tumors reached 100 mm$^3$, mice were treated with a single dose of a click radiolabeled anti-PSMA mAb ("PSMB127") actinium radioconjugate according to an embodiment of the application at a range of activities or the isotype control, a human IgG4 antibody that binds to a viral target absent in this system radioconjugate; in particular.
Figure 5B:
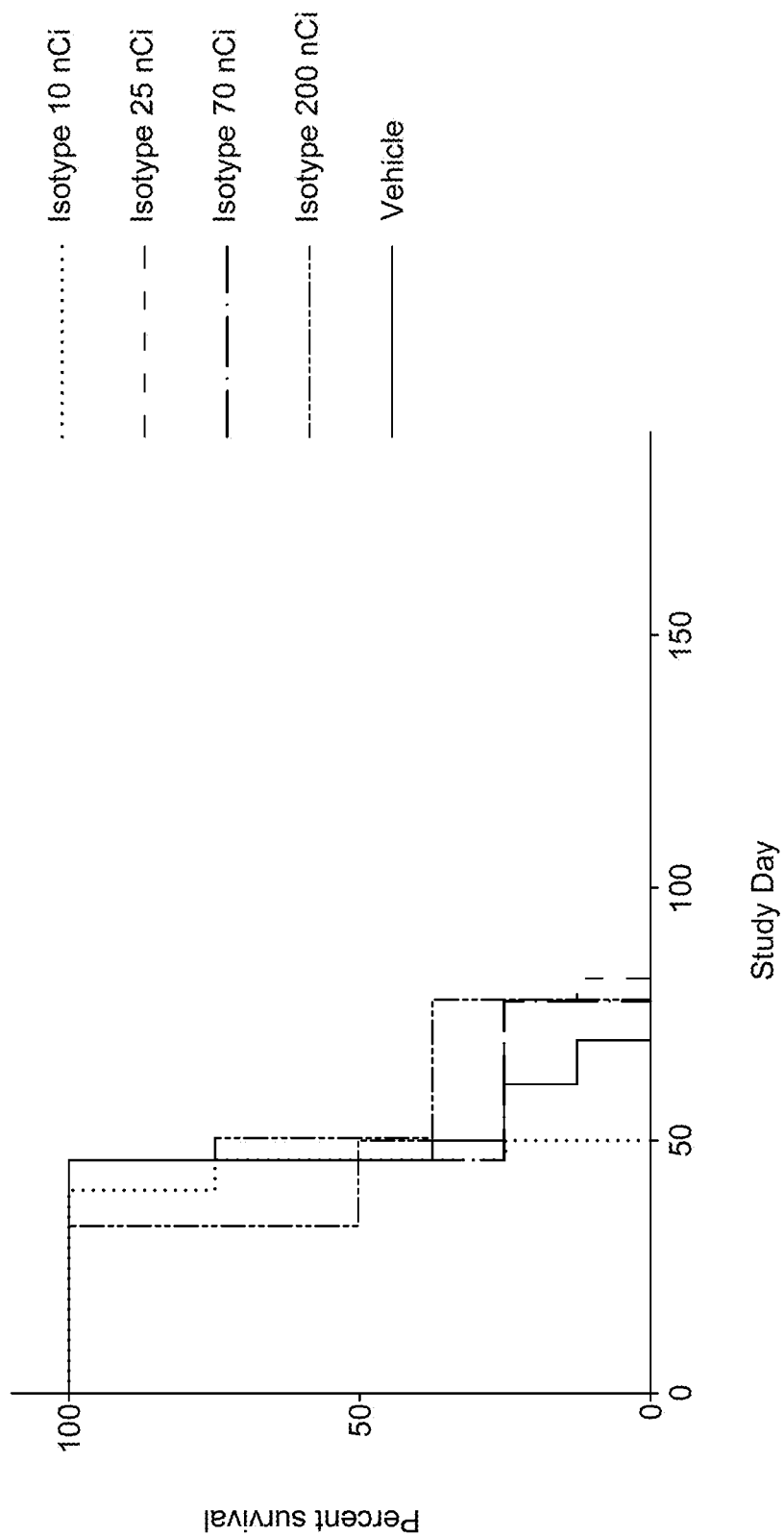
FIG. 5B shows results of a mouse tumor xenograft study; mice were implanted with human prostate cancer LNCaP cells; when tumors reached 100 mm³, mice were treated with a single dose of a click radiolabeled anti-PSMA mAb ("PSMB127") actinium radioconjugate according to an embodiment of the application at a range of activities or the isotype control, a human IgG4 antibody that binds to a viral target absent in this system radioconjugate; in particular.
Figure 5C:
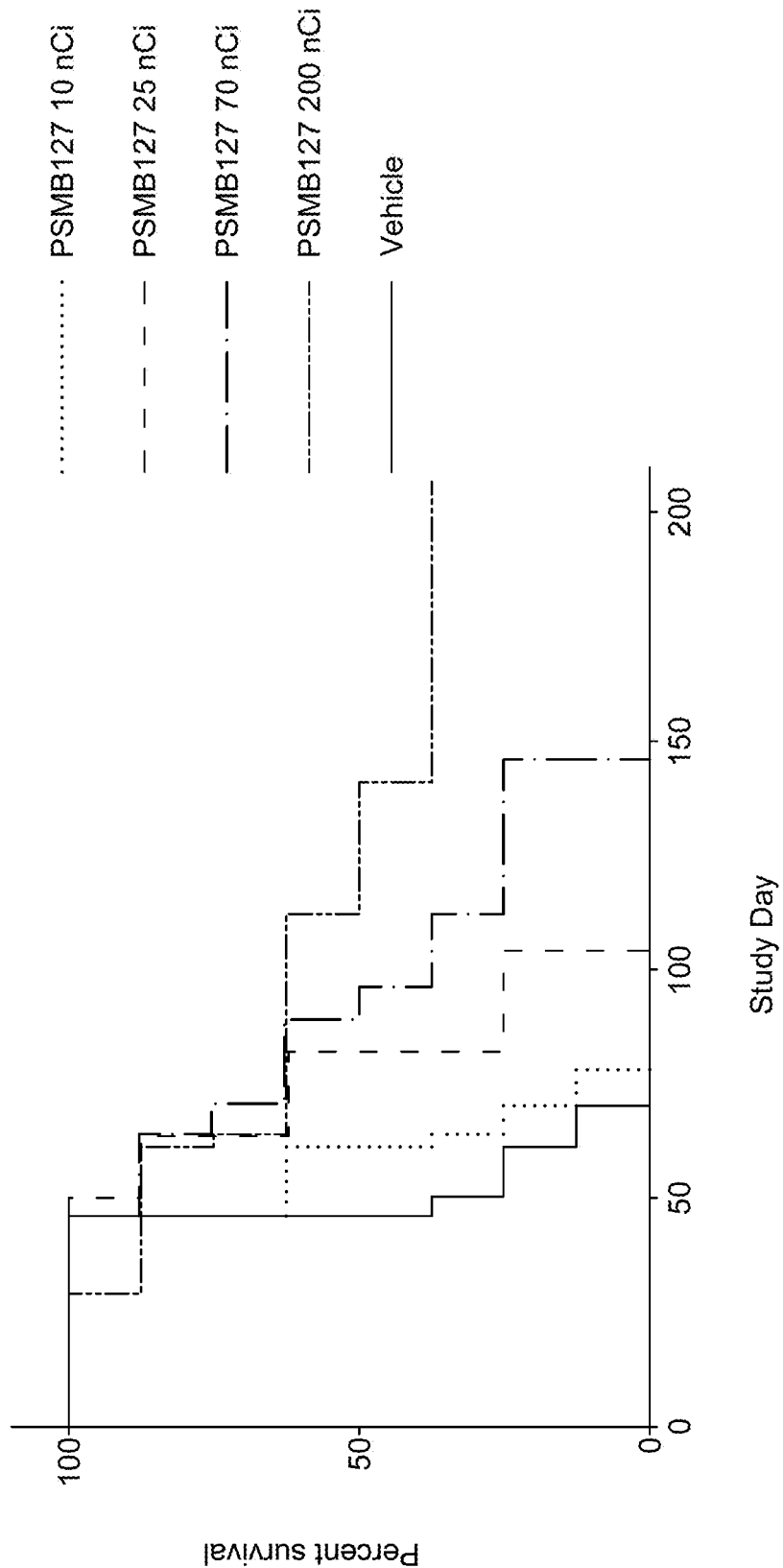
FIG. 5C shows results of a mouse tumor xenograft study; mice were implanted with human prostate cancer LNCaP cells; when tumors reached 100 mm³, mice were treated with a single dose of a click radiolabeled anti-PSMA mAb ("PSMB127") actinium radioconjugate according to an embodiment of the application at a range of activities or the isotype control, a human IgG4 antibody that binds to a viral target absent in this system radioconjugate; in particular.

Anti-PSMA mAb-DOTA-Ac-225 shows tumor growth inhibition after a single dose, particularly at the higher radioactive doses, and superior to isotype control at all doses (FIG. 5A). All doses of the control mAb radioconjugate had similar survival curves to the vehicle control (FIG. 5B; Table 7); the anti-PSMA mAb conjugate showed a clear dose-response with survival increasing with increasing radioactive dose (FIG. 5C; Table 7). The study was terminated after 209 days, with 3 mice remaining, all from the anti-PSMA mAb 200 nCi group and showing no detectable tumors.

TABLE 7

| | Median survival | |
| --- | --- | --- |
| Dose | anti-PSMA mAb | Isotype control |
| 10 nCi | 61 d | 46 d |
| 25 nCi | 82 d | 48 d |
| 70 nCi | 92.5 d | 50 d |
| 200 nCi | 126.5 d | 39.5 d |
| Vehicle | | 46 |

The embodiments of the invention are intended to be merely exemplary, and those skilled in the art will recognize, or be able to ascertain using no more than routine experimentation, numerous equivalents to the specific procedures of the invention. All such equivalents are considered to be within the scope of the present invention and are covered by the following claims.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

We claim:

1. A method of labeling a polypeptide with a radiometal ion, the method comprising:
   a. providing an antibody or an antigen binding fragment thereof that is covalently linked to a first click reaction partner, wherein the first click reaction partner comprises an azide, and wherein the antibody or antigen binding fragment thereof that is covalently linked to a first click reaction partner is obtained by a site-specific incorporation of the first click reaction partner through a reaction with an azide-labeled sugar or an azido amine;
   b. providing a radiocomplex comprising the radiometal ion and a chelating moiety coordinated with the radiometal ion, wherein the chelating moiety comprises a chelant covalently linked to a second click reaction partner, wherein the second click reaction partner comprises a strained alkyne group; and
   c. contacting the antibody or antigen binding fragment thereof that is covalently linked to a first click reaction partner with the radiocomplex, wherein the contacting is performed without a copper catalyst, to allow the first click reaction partner to react with the second click reaction partner to thereby label the antibody or an antigen binding fragment thereof with the radiometal ion;
   wherein the chelant comprises a macrocycle having the structure of formula (I):

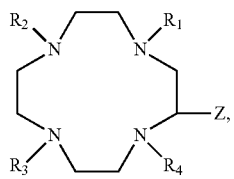

formula (I)

wherein each of $R_1$, $R_2$, $R_3$ and $R_4$ is independently $CHQCO_2X$, wherein
Q is independently hydrogen, $C_1$-$C_4$ alkyl or ($C_1$-$C_2$ alkyl) phenyl, and
X is independently hydrogen, benzyl, $C_1$-$C_4$ alkyl; and
Z is $(CH_2)_n$ Y, wherein
n is 1-10, and
Y is a linker that covalently links the second click reaction partner and the chelant, and wherein Y is a bond, C(O)—$(CH_2)_m$—C(O), $(CH_2)_p$—C(O)—NH—$(CH_2)_q$—C(O), (O—$CH_2$—$CH_2)_r$—O, $(CH_2)_p$[C(O)—NH—$(CH_2)_q]_t$, $(CH_2)_p$—S—S—$(CH_2)_q$, or valine-citrulline-PAB, wherein p=0-4, q=1-4, r=1-4, t=1-3, m=1-4;
alternatively, Z is hydrogen; and, when Z is hydrogen then
each of $R_1$, $R_2$, $R_3$ and $R_4$ is independently $CHQCO_2X$, wherein
Q is a linker that covalently links the second click reaction partner and the chelant, and
wherein Q is a bond, C(O)—$(CH_2)_m$—C(O), $(CH_2)_p$—C(O)—NH—$(CH_2)_q$—C(O), (O—$CH_2$—$CH_2)_r$—O, $(CH_2)_p$[C(O)—NH—$(CH_2)_q]_t$, $(CH_2)_p$—S—S—$(CH_2)_q$, or valine-citrulline-PAB,
wherein p=0-4, q=1-4, r=1-4, t=1-3, and
X is independently hydrogen, benzyl, or $C_1$-$C_4$ alkyl;
or alternatively, the chelant comprises deferoxamine-YY, wherein YY is a linker that covalently links the second click reaction partner and the chelant, and wherein YY is a bond, C(O)—$(CH_2)_m$—C(O), $(CH_2)_p$—C(O)—NH—$(CH_2)_q$—C(O), (O—$CH_2$—$CH_2)_r$—O, $(CH_2)_p$[C(O)—NH—$(CH_2)_q]_t$, $(CH_2)_p$—S—S—$(CH_2)_q$, or valine-citrulline-PAB, wherein p=0-4, q=1-4, r=1-4, t=1-3.

2. The method of claim 1, wherein the antibody is an antibody that binds to human prostate-specific membrane antigen (PSMA) or an antigen binding fragment thereof, comprising a heavy chain (HC) complementarity-determining region(CDR)1 sequence of SEQ ID NO: 3, a HC CDR2 sequence of SEQ ID NO: 4, a HC CDR3 sequence of SEQ ID NO: 5, a light chain (LC) CDR1 sequence of SEQ ID NO: 6, a LC CDR2 sequence of SEQ ID NO: 7, and a LC CDR3 sequence of SEQ ID NO:8.

3. The method of claim 1, wherein the radiometal ion is $^{225}$Ac, $^{111}$In or $^{89}$Zr.

4. The method of claim 1, wherein the antibody or antigen binding fragment thereof that is covalently linked to a first click reaction partner is obtained by a method comprising trimming an antibody or antigen binding fragment thereof with a bacterial endoglycosidase specific for the β-1,4 linkage between a core GlcNac residue in a Fc-glycosylation site of the antibody to obtain a trimmed antibody or antigen binding fragment thereof, and reacting the trimmed antibody or antigen binding fragment thereof with an azide-labeled sugar, in the presence of a sugar transferase to thereby obtain the antibody or antigen binding fragment thereof that is covalently linked to the first click reaction partner.

5. The method of claim 4 wherein the azide-labeled sugar is UDP-N-azidoacetylgalactosamine (UDP-GalNaz) or UDP-6-azido 6-deoxy GalNAc.

6. The method of claim 4 wherein the sugar transferase is GalT galactosyltransferase or GalNAc transferase.

7. The method of claim 1, wherein the antibody or antigen binding fragment thereof that is covalently linked to a first click reaction partner is obtained by a method comprising deglycosylating an antibody or antigen binding fragment thereof with an amidase to obtain a deglycosylated antibody or antigen binding fragment thereof, and reacting the deglycosylated antibody or antigen binding fragment thereof with an azido amine in the presence of a microbial transglutaminase to thereby obtain the polypeptide that is covalently linked to a first click reaction partner.

8. The method of claim 7 wherein the azido amine is selected from 3-azido propylamine, 6-azido hexylamine, O-(2-Aminoethyl)-O'-(2-azidoethyl)tetraethylene glycol, O-(2-Aminoethyl)-O'-(2-azidoethyl)pentaethylene glycol, and O-(2-Aminoethyl)-O'-(2-azidoethyl)triethylene glycol.

9. The method of claim 1, wherein the chelating moiety comprises the structure of formula (II):

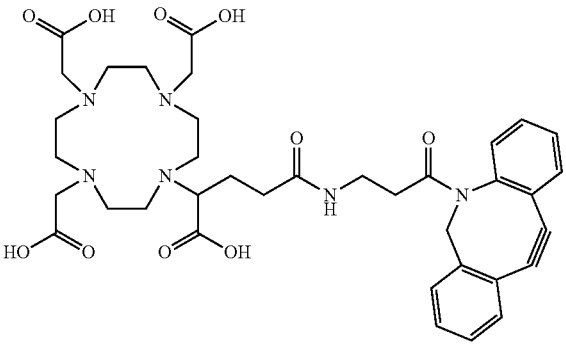

formula (II)

or the structure of formula (III):

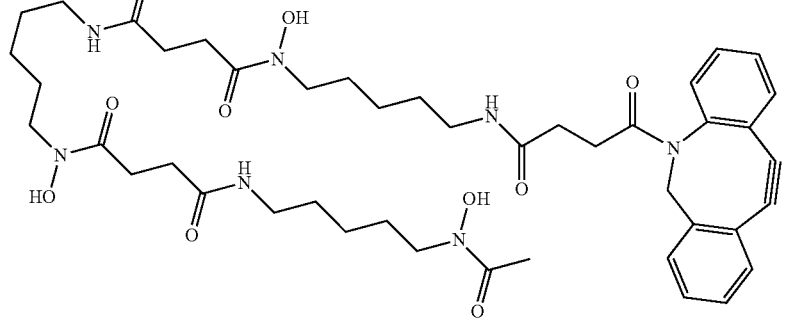

formula (III)

10. The method of claim 3, wherein the antibody or antigen binding fragment thereof that is covalently linked to the first click reaction partner is obtained by a method comprising trimming an antibody or antigen binding fragment thereof with a bacterial endoglycosidase specific for the β-1,4 linkage between a core GlcNac residue in a Fc-glycosylation site of the antibody to obtain a trimmed antibody or antigen binding fragment thereof, and reacting the trimmed antibody or antigen binding fragment thereof with an azide-labeled sugar in the presence of a sugar transferase, to thereby obtain the modified antibody or antigen binding fragment thereof that is covalently linked to the first click reaction partner.

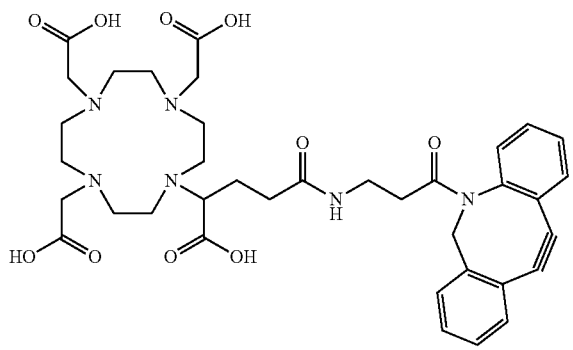

formula (II)

or the structure of formula (III):

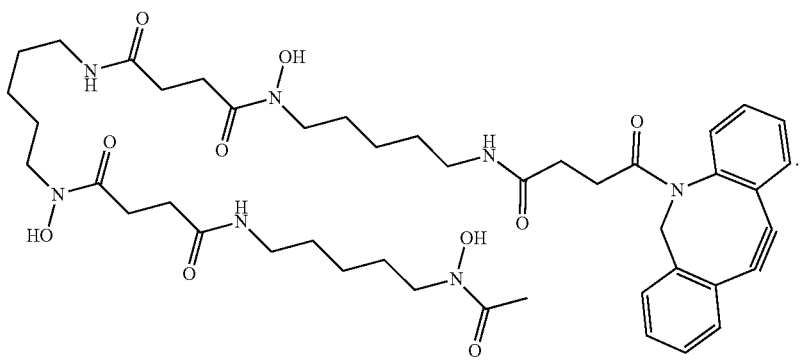

formula (III)

11. The method of claim 10 wherein the azide labeled sugar is UDP-N-azidoacetylgalactosamine (UDP-GalNaz) or UDP-6-azido 6-deoxy GalNAc.

12. The method of claim 10 wherein the sugar transferase is selected from GalT galactosyltransferase or GalNAc transferase.

13. The method of claim 3, wherein the antibody or antigen binding fragment thereof that is covalently linked to the first click reaction partner is obtained by a method comprising deglycosylating an antibody or antigen binding fragment thereof with an amidase to obtain a deglycosylated antibody or antigen binding fragment thereof, and reacting the deglycosylated antibody or antigen binding fragment thereof with an azido amine, in the presence of a microbial transglutaminase to thereby obtain the modified antibody or antigen binding fragment thereof that is covalently linked to the first click reaction partner.

14. The method of claim 13 wherein the azido amine is selected from 3-azido propylamine, 6-azido hexylamine, O-(2-Aminoethyl)-O'-(2-azidoethyl)tetraethylene glycol, O-(2-Aminoethyl)-O'-(2-azidoethyl)pentaethylene glycol, and O-(2-Aminoethyl)-O'-(2-azidoethyl)triethylene glycol.

15. The method of claim 3, wherein the chelating moiety comprises the structure of formula (II):

16. A pharmaceutical composition comprising a radiolabeled polypeptide prepared by a method of claim 1 and a pharmaceutically acceptable carrier.

17. A theranostic agent comprising a radiolabeled antibody prepared by a method of claim 1 and a pharmaceutically acceptable carrier, wherein the immunological properties of the radiolabeled antibody are preserved.

18. A theranostic agent prepared by the method of claim 1 having a structure of formula (VIII):

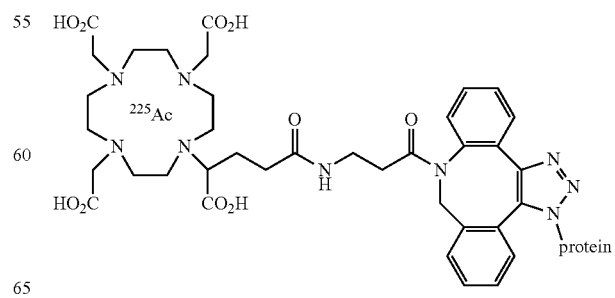

or formula (IX):

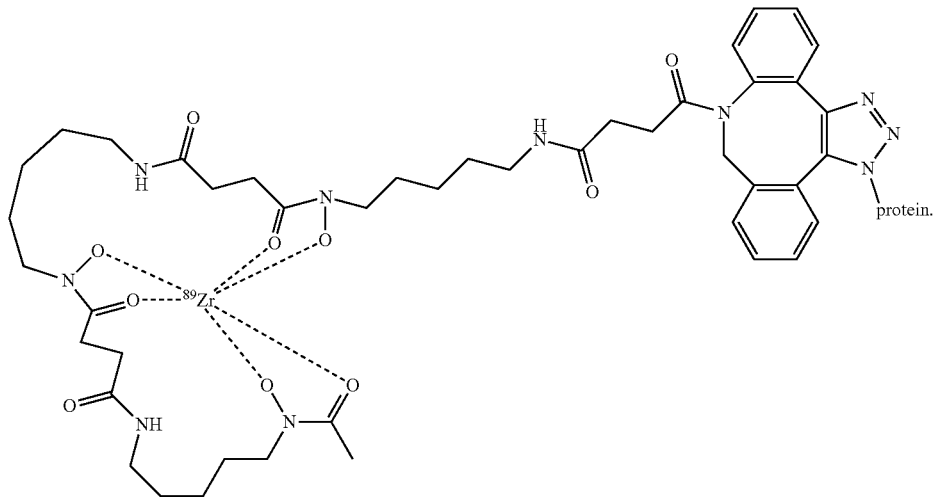

19. The theranostic agent of claim 17 wherein the radiometal ion is selected from $^{32}$P, $^{47}$Sc, $^{67}$Cu, $^{77}$As, $^{89}$Sr, $^{90}$Y, $^{99}$Tc, $^{105}$Rh, $^{109}$Pd, $^{111}$Ag, $^{131}$I, $^{153}$Sm, $^{159}$Gd, $^{165}$Dy, $^{166}$Ho, $^{169}$Er, $^{177}$Lu, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{225}$Ac, $^{255}$Fm, $^{227}$Th, $^{62}$Cu, $^{64}$Cu, $^{67}$Ga, $^{68}$Ga, $^{86}$Y, $^{89}$Zr, or $^{111}$In.

20. The method of claim 3, wherein the antibody is an antibody that binds to human prostate-specific membrane antigen (PSMA) or an antigen binding fragment thereof, comprising a heavy chain (HC) complementarity-determining region(CDR)1 sequence of SEQ ID NO: 3, a HC CDR2 sequence of SEQ ID NO: 4, a HC CDR3 sequence of SEQ ID NO: 5, a light chain (LC) CDR1 sequence of SEQ ID NO: 6, a LC CDR2 sequence of SEQ ID NO: 7, and a LC CDR3 sequence of SEQ ID NO:8.

21. The method of claim 1, wherein
when the antibody or antigen binding fragment thereof that is covalently linked to a first click reaction partner is obtained through a reaction with an azide-labeled sugar, then the antibody or antigen binding fragment thereof that is covalently linked to a first click reaction partner is obtained by a method comprising trimming an antibody or antigen binding fragment thereof with a bacterial endoglycosidase specific for the ß-1,4 linkage between a core GlcNac residue in a Fc-glycosylation site of the antibody to obtain a trimmed antibody or antigen binding fragment thereof, and reacting the trimmed antibody or antigen binding fragment thereof with an azide-labeled sugar, in the presence of a sugar transferase; wherein the azide-labeled sugar is UDP-N-azidoacetylgalactosamine (UDP-GalNaz) or UDP-6-azido 6-deoxy GalNAc, and the sugar transferase is GalT galactosyltransferase or GalNAc transferase; and
when the antibody or antigen binding fragment thereof that is covalently linked to a first click reaction partner is obtained through a reaction with an azido amine, then the antibody or antigen binding fragment thereof that is covalently linked to a first click reaction partner is obtained by a method comprising deglycosylating an antibody or antigen binding fragment thereof with an amidase to obtain a deglycosylated antibody or antigen binding fragment thereof, and reacting the deglycosylated antibody or antigen binding fragment thereof with an azido amine in the presence of a microbial transglutaminase, wherein the azido amine is selected from 3-azido propylamine, 6-azido hexylamine, O-(2-Aminoethyl)-O'-(2-azidoethyl)tetraethylene glycol, O-(2-Aminoethyl)-O'-(2-azidoethyl)pentaethylene glycol, and O-(2-Aminoethyl)-O'-(2-azidoethyl)triethylene glycol;
wherein the chelating moiety comprises the structure of formula (II):

formula (II)

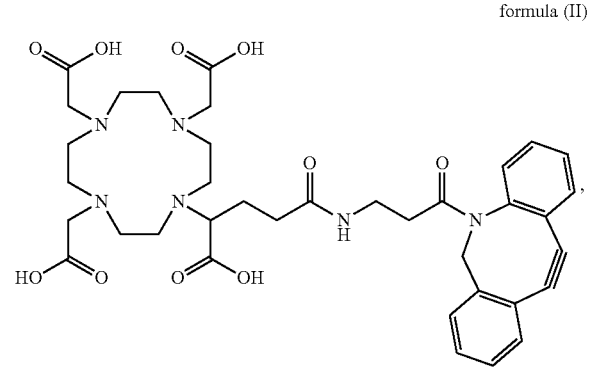 [SMILES: O=C(O)CN1CCN(CC(=O)O)CCN(C(CCC(=O)NCCC(=O)N2Cc3ccccc3C#Cc3ccccc32)C(=O)O)CCN(CC(=O)O)CC1]

or the structure of formula (III):
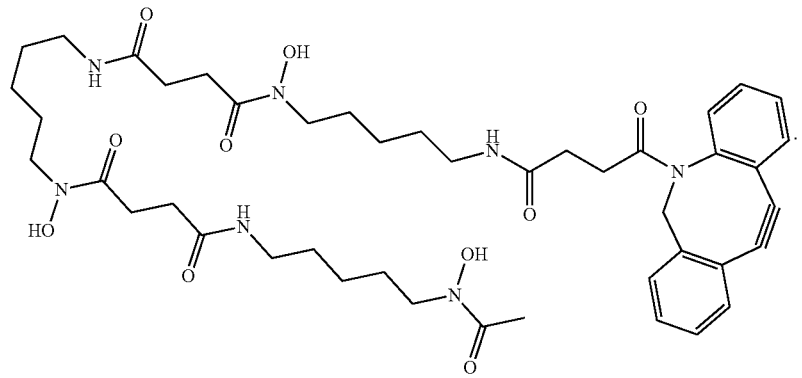
Formula (III)
22. The method of claim 21, wherein the radiometal ion is a diagnostic emitter.
23. The method of claim 21, wherein the radiometal ion is a therapeutic emitter.

SEQUENCE LISTING

<160> NUMBER OF SEQ ID NOS: 10

<210> SEQ ID NO 1
<211> LENGTH: 447
<212> TYPE: PRT
<213> ORGANISM: Artificial Sequence
<220> FEATURE:
<223> OTHER INFORMATION: Control mAb HC

<400> SEQUENCE: 1

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu

```
              355                 360                 365
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 2
<211> LENGTH: 219
<212> TYPE: PRT
<213> ORGANISM: Artificial Sequence
<220> FEATURE:
<223> OTHER INFORMATION: Control mAb LC

<400> SEQUENCE: 2

Asp Ile Val Met Thr Gln Ser Pro Asp Ser Leu Ala Val Ser Leu Gly
1               5                   10                  15

Glu Arg Asn Ala Thr Ile Asn Cys Arg Ala Ser Gln Ser Val Asp Tyr
            20                  25                  30

Asn Gly Ile Ser Tyr Met His Trp Tyr Gln Gln Lys Pro Gly Gln Pro
        35                  40                  45

Pro Lys Leu Leu Ile Tyr Ala Ala Ser Asn Pro Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Ile
                85                  90                  95

Ile Glu Asp Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 3
<211> LENGTH: 5
<212> TYPE: PRT
<213> ORGANISM: Artificial Sequence
<220> FEATURE:
<223> OTHER INFORMATION: Anti-PSMA mAb (PSMB127) HC CDR1

<400> SEQUENCE: 3
```

```
Ser Asp Ala Met His
1               5

<210> SEQ ID NO 4
<211> LENGTH: 17
<212> TYPE: PRT
<213> ORGANISM: Artificial Sequence
<220> FEATURE:
<223> OTHER INFORMATION: Anti-PSMA mAb (PSMB127) HC CDR2

<400> SEQUENCE: 4

Glu Ile Ser Gly Ser Gly Gly Tyr Thr Asn Tyr Ala Asp Ser Val Lys
1               5                   10                  15

Gly

<210> SEQ ID NO 5
<211> LENGTH: 15
<212> TYPE: PRT
<213> ORGANISM: Artificial Sequence
<220> FEATURE:
<223> OTHER INFORMATION: Anti-PSMA mAb (PSMB127) HC CDR3

<400> SEQUENCE: 5

Asp Ser Tyr Asp Ser Ser Leu Tyr Val Gly Asp Tyr Phe Asp Tyr
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Anti-PSMA mAb (PSMB127) LC CDR1

<400> SEQUENCE: 6

Arg Ala Ser Gln Ser Val Ser Ser Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Anti-PSMA mAb (PSMB127) LC CDR2

<400> SEQUENCE: 7

Asp Ala Ser Asn Arg Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Anti-PSMA mAb (PSMB127) LC CDR3

<400> SEQUENCE: 8

Gln Gln Arg Ser Asn Trp Pro Leu Thr
1               5

<210> SEQ ID NO 9
<211> LENGTH: 451
<212> TYPE: PRT
<213> ORGANISM: Artificial Sequence
<220> FEATURE:
<223> OTHER INFORMATION: Anti-PSMA mAb (PSMB127) HC

<400> SEQUENCE: 9
```

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415
```

-continued

```
Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: Anti-PSMA mAb (PSMB127) LC

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```